United States Patent
Hayashida et al.

(10) Patent No.: US 11,172,981 B2
(45) Date of Patent: Nov. 16, 2021

(54) TREATMENT SYSTEM, CONTROL DEVICE AND TREATMENT METHOD

(71) Applicant: OLYMPUS CORPORATION, Hachioji (JP)

(72) Inventors: Tsuyoshi Hayashida, Hachioji (JP); Satomi Sakao, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 490 days.

(21) Appl. No.: 16/163,747

(22) Filed: Oct. 18, 2018

(65) Prior Publication Data

US 2019/0046262 A1  Feb. 14, 2019

Related U.S. Application Data

(63) Continuation of application No. PCT/JP2016/063089, filed on Apr. 26, 2016.

(51) Int. Cl.
*A61B 18/12* (2006.01)
*A61B 18/14* (2006.01)
(Continued)

(52) U.S. Cl.
CPC .. *A61B 18/1445* (2013.01); *A61B 17/320092* (2013.01); *A61B 18/085* (2013.01);
(Continued)

(58) Field of Classification Search
CPC .......... A61B 17/320092; A61B 18/085; A61B 18/1206; A61B 18/1445; A61B 18/18; A61B 2018/0019; A61B 2018/00404; A61B 2018/00607; A61B 2018/00642; A61B 2018/00678; A61B 2018/00708; A61B 2018/1273
See application file for complete search history.

(56) References Cited

U.S. PATENT DOCUMENTS

| | | |
|---|---|---|
| 5,702,390 A | 12/1997 | Austin et al. |
| 5,944,718 A | 8/1999 | Austin et al. |

(Continued)

FOREIGN PATENT DOCUMENTS

| | | |
|---|---|---|
| JP | H10-199 A | 1/1998 |
| WO | 2012/061638 A1 | 5/2012 |

OTHER PUBLICATIONS

Jul. 19, 2016 International Search Report issued in International Patent Application No. PCT/JP2016/063089.
(Continued)

*Primary Examiner* — Daniel W Fowler
(74) *Attorney, Agent, or Firm* — Oliff PLC

(57) ABSTRACT

In a treatment system, an energy treatment instrument includes a pair of grasping pieces closing with respect to each other. An energy output source outputs electric energy to the energy treatment instrument, thereby applying treatment energy to a treatment target grasped between the grasping pieces. A processor creates an optical flow of the treatment target observed by an observation element, and switches an actuation state of the energy treatment instrument between a first mode for treating the treatment target and a second mode for treating the treatment target that is different from the first mode, based on the optical flow.

15 Claims, 13 Drawing Sheets

(51) Int. Cl.
 *A61B 17/32* (2006.01)
 *A61B 18/08* (2006.01)
 *A61B 18/18* (2006.01)
 *A61B 18/00* (2006.01)
 *A61B 90/00* (2016.01)
 *A61B 17/28* (2006.01)
 *A61B 17/00* (2006.01)

(52) U.S. Cl.
 CPC .......... *A61B 18/1206* (2013.01); *A61B 18/18* (2013.01); *A61B 90/361* (2016.02); *A61B 2017/00026* (2013.01); *A61B 2017/00075* (2013.01); *A61B 2017/2825* (2013.01); *A61B 2018/0019* (2013.01); *A61B 2018/00404* (2013.01); *A61B 2018/00607* (2013.01); *A61B 2018/00642* (2013.01); *A61B 2018/00678* (2013.01); *A61B 2018/00708* (2013.01); *A61B 2018/00761* (2013.01); *A61B 2018/00875* (2013.01); *A61B 2018/00982* (2013.01); *A61B 2018/00994* (2013.01); *A61B 2018/1273* (2013.01); *A61B 2090/065* (2016.02)

(56) References Cited

U.S. PATENT DOCUMENTS

2002/0128650 A1* 9/2002 McClurken ........ A61B 18/1442
 606/48
2003/0212420 A1 11/2003 Gruhl et al.
2015/0251024 A1* 9/2015 Belt .................... A61N 7/00
 600/439

OTHER PUBLICATIONS

Nov. 5, 2019 Office Action issued in Japanese Patent Application No. 2018-513994.
Oct. 30, 2018 International Preliminary Report on Patentability issued in International Patent Application No. PCT/JP2016/063089.

* cited by examiner

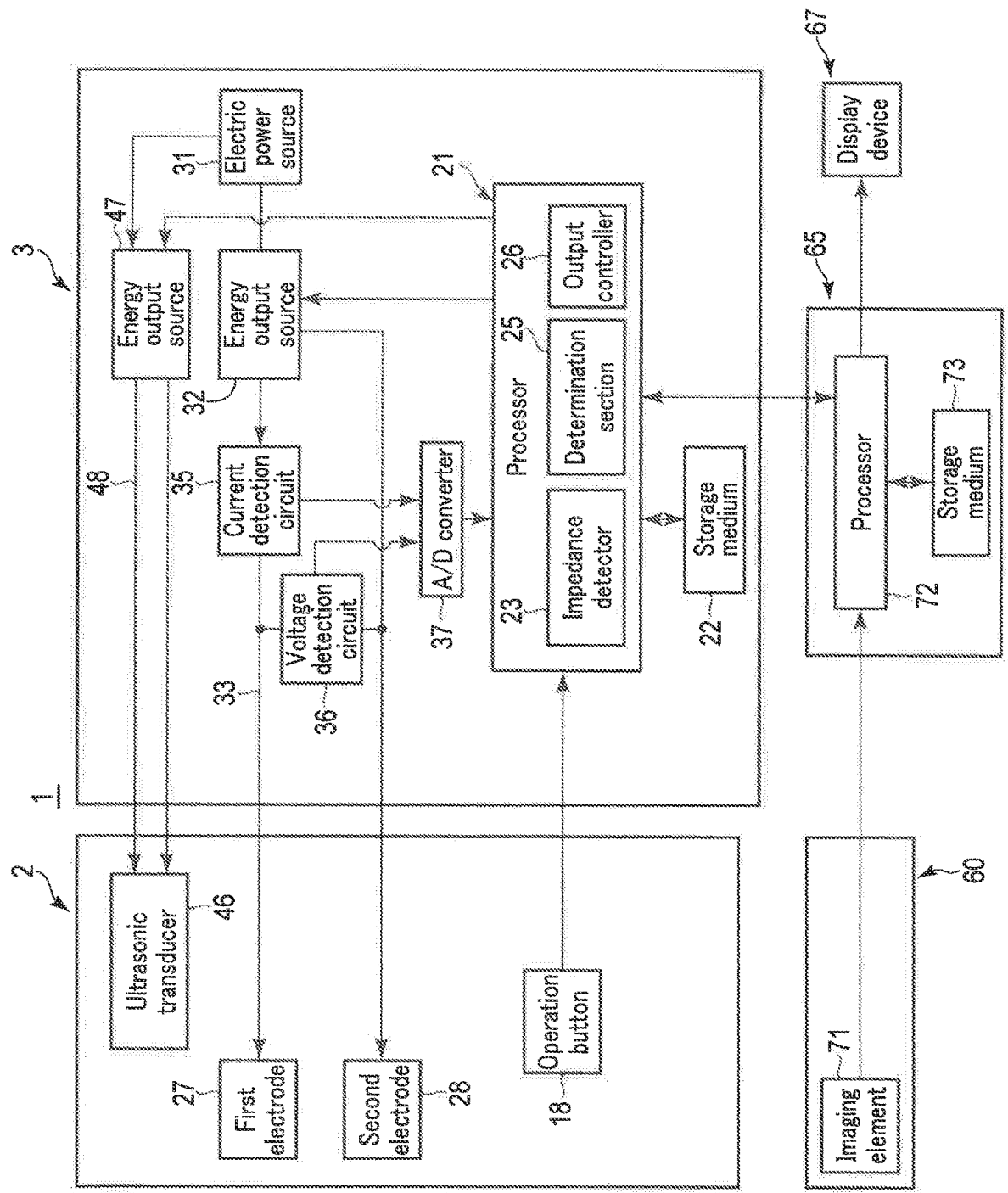
F I G. 2

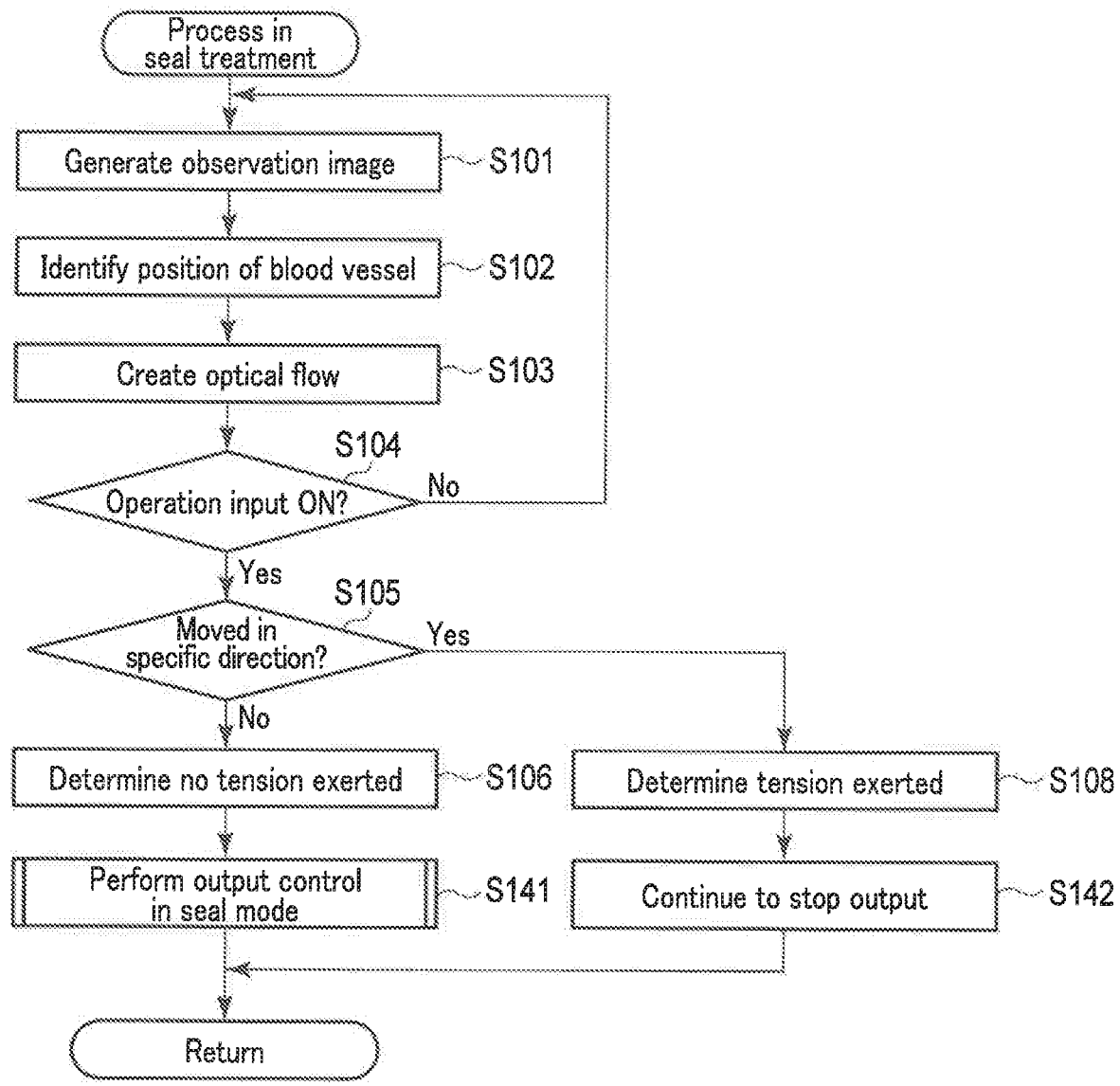
F I G. 12

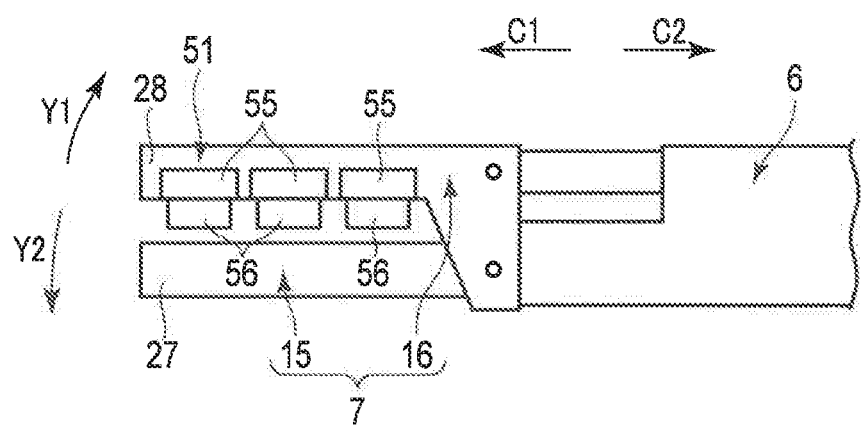
F I G. 14

TREATMENT SYSTEM, CONTROL DEVICE AND TREATMENT METHOD

CROSS-REFERENCE TO RELATED APPLICATIONS

This is a Continuation Application of PCT Application No. PCT/JP2016/063089, filed Apr. 26, 2016, the entire contents of which are incorporated herein by reference.

BACKGROUND OF THE INVENTION

1. Field of the Invention

The present invention relates to a treatment system including an energy treatment instrument which applies treatment energy to a treatment target grasped between a pair of grasping pieces, and relates to a control device for controlling a medical instrument and treatment method.

2. Description of the Related Art

PCT International Publication No. 2012/061638 discloses an energy treatment instrument which grasps a treatment target, such as a biological tissue, between a pair of grasping pieces. In this energy treatment instrument, the grasping pieces are respectively provided with electrodes. When electric energy is supplied to both electrodes, a high-frequency current flows between the electrodes through the grasped treatment target. The high-frequency current is thereby applied as treatment energy to the treatment target.

BRIEF SUMMARY OF THE INVENTION

According to one aspect of the invention, a treatment system includes that: an energy treatment instrument, the energy treatment instrument including a first grasping piece, and a second grasping piece configured to close with respect to the first grasping piece and grasp a treatment target together with the first grasping piece; an energy output source configured to output electric energy that is to be supplied to the energy treatment instrument, and configured to supply the electric energy to the energy treatment instrument, thereby applying treatment energy to the treatment target grasped between the first grasping piece and the second grasping piece; an observation element configured to observe the grasped treatment target; and a processor configured to create an optical flow of the treatment target observed by the observation element, and configured to switch an actuation state of the energy treatment instrument between a first mode for treating the treatment target and a second mode for treating the treatment target that is different from the first mode, based on the optical flow.

According to one another aspect of the invention, a control device for controlling a medical instrument, the medical instrument including a pair of grasping pieces configured to open and close with respect to each other, the control device being configured to: determine whether there is tension exerted on a treatment target grasped by the pair of grasping pieces based on an optical flow of a treatment target observed by an observation element; select, based on a determination result, a control mode from a first mode, which is adopted when there is no tension exerted on the treatment target, and a second mode, which is adopted when there is tension; and control the medical instrument based on the selected control mode.

According to one another aspect of the invention, a treatment method, comprising: by use of an energy treatment instrument, which includes a first grasping piece, and a second grasping piece configured to open and close with respect to the first grasping piece, grasping a treatment target between the first grasping piece and the second grasping piece; outputting electric energy that is to be supplied to the energy treatment instrument, and applying treatment energy to the treatment target grasped between the first grasping piece and the second grasping piece; and creating an optical flow of the treatment target by use of an observation element, and switching an actuation state of the energy treatment instrument between a first mode for treating the treatment target and a second mode for treating the treatment target that is different from the first mode, based on the optical flow.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram illustrating a control configuration in the treatment system according to the first embodiment;

FIG. 12 is a flowchart illustrating a process executed by the processor in the seal treatment of the blood vessel using the treatment system according to the fourth modification of the first embodiment;

FIG. 14 is a schematic diagram illustrating an example of a grasping force adjustment element according to the second embodiment.

DETAILED DESCRIPTION OF THE INVENTION

First Embodiment

Figure 1:
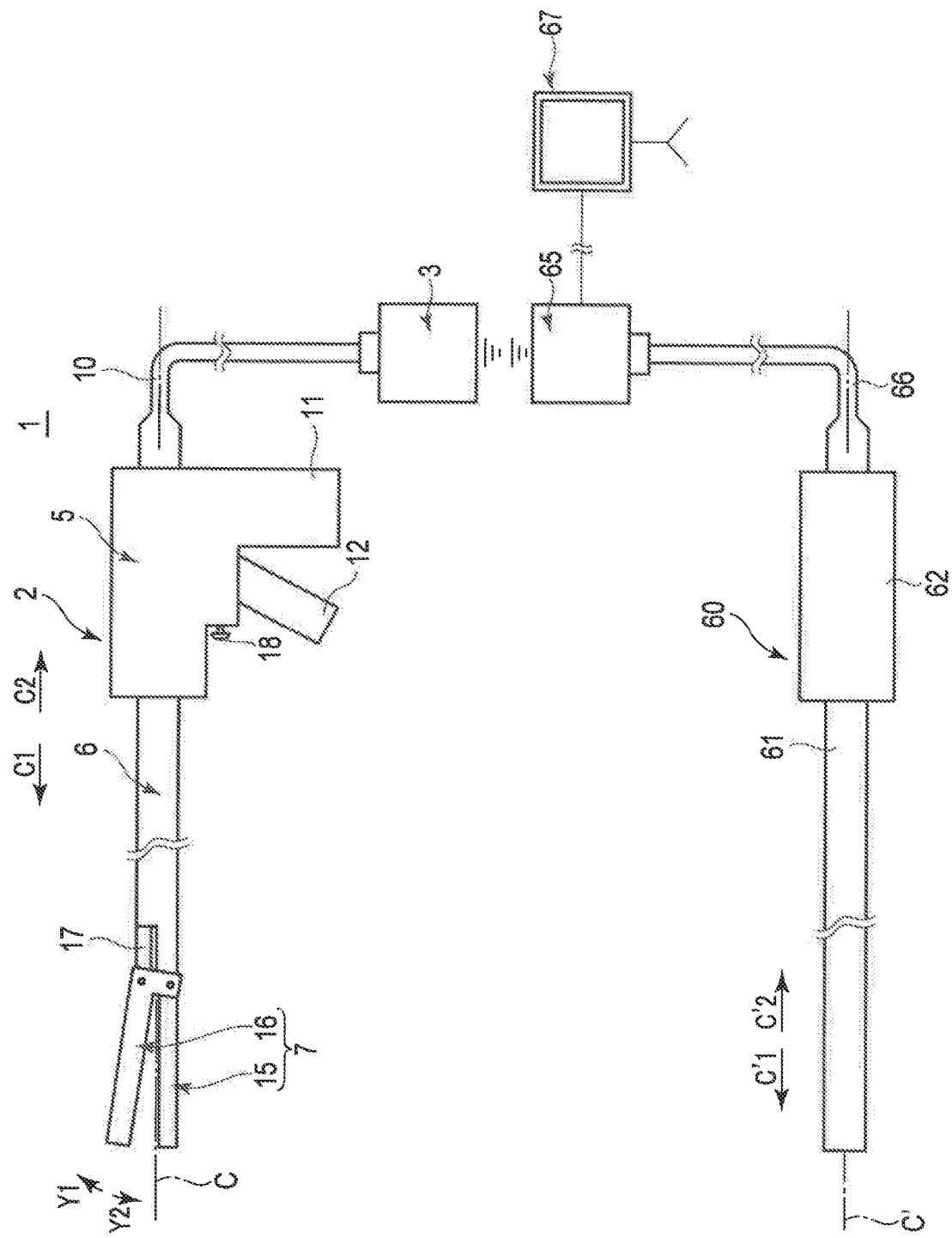
FIG. 1 is a schematic diagram illustrating a treatment system according to a first embodiment.

A first embodiment of the present invention will be described with reference to FIGS. 1 to 7. FIG. 1 is a diagram illustrating a treatment system 1 according to the present embodiment. As illustrated in FIG. 1, the treatment system 1 includes an energy treatment instrument 2 and a control device (energy control device) 3. The energy treatment instrument 2 has a longitudinal axis C. Here, in the energy treatment instrument 2, one side of a direction along the longitudinal axis C is defined as a distal side (arrow C1 side), and the side opposite to the distal side is defined as a proximal side (arrow C2 side).

The energy treatment instrument 2 includes a housing 5 which can be hand-held, a sheath (shaft) 6 coupled to the distal side of the housing 5, and an end effector 7 provided in a distal portion of the sheath 6. One end of a cable 10 is connected to the housing 5 of the energy treatment instrument 2. The other end of the cable 10 is detachably connected to the control device 3. The housing 5 is provided with a grip (stationary handle) 11, and a handle (movable handle) 12 is rotatably attached to the housing 5. In accordance with the handle 12 rotating relative to the housing 5, the handle 12 opens or closes relative to the grip 11. According to the present embodiment, the handle 12 is located on the distal side with respect to the grip 11, and the handle 12 moves substantially in parallel to the longitudinal axis C in the opening or closing motion relative to the grip 11. The embodiment, however, is not limited thereto. In one example, the handle 12 may be located on the proximal side with respect to the grip 11. In another example, the handle 12 may be located on the side opposite to the grip 11 with respect to the longitudinal axis C, and a moving direction in the opening or closing motion relative to the grip 11 may intersect with the longitudinal axis C (may be substantially perpendicular to the longitudinal axis C).

The sheath 6 extends along the longitudinal axis C. The end effector 7 includes a first grasping piece 15 and a second grasping piece 16, which is configured to open and close relative to the first grasping piece 15. The handle 12 and end effector 7 are coupled via a movable member 17 that extends inside the sheath 6 along the longitudinal axis C. By opening or closing the handle 12, which is an opening and closing operation input section, relative to the grip 11, the movable member 17 moves along the longitudinal axis C relative to the sheath 6 and housing 5, thereby opening or closing the pair of grasping pieces 15 and 16 relative to each other. When the grasping pieces 15 and 16 are closed relative to each other, the grasping pieces 15 and 16 grasp a biological tissue, such as a blood vessel, as a treatment target. The opening and closing directions (directions of arrow Y1 and arrow Y2) of the grasping pieces 15 and 16 intersect the longitudinal axis C (i.e., they are substantially perpendicular to the longitudinal axis C).

The end effector 7 will suffice as long as the paired grasping pieces 15 and 16 can open or close relative to each other in accordance with the opening or closing motion of the handle 12. In one example, one of the grasping pieces 15 and 16 is formed integrally with the sheath 6 or fixed to the sheath 6, while the other one of the grasping pieces 15 and 16 is pivotally attached to the distal portion of the sheath 6. In another example, both of the grasping pieces 15 and 16 are pivotally attached to the distal portion of the sheath 6. In still another example, a rod member (not shown) is inserted through the sheath 6, and a portion of the rod member (probe) projecting from the sheath 6 toward the distal side forms one of the grasping pieces 15 and 16. The other one of the grasping pieces 15 and 16 is pivotally attached to the distal portion of the sheath 6. In still another example, a rotary knob (not shown) may be attached to the housing 5. If this is the case, by turning the rotary knob relative to the housing 5 around the longitudinal axis C relative to the housing 5, the sheath 6 and the end effector 7 turn together with the rotary knob around the longitudinal axis C relative to the housing 5. In this manner, the angular position of the end effector 7 around the longitudinal axis C can be adjusted.

FIG. 2 is a diagram illustrating a control configuration in the treatment system 1. As illustrated in FIG. 2, the control device 3 includes a processor (controller) 21, which controls the entire treatment system 1, and a storage medium 22. The processor 21 is formed of an integrated circuit including a Central Processing Unit (CPU), an Application Specific Integrated Circuit (ASIC), or a Field Programmable Gate Array (FPGA). The processor 21 may be formed of a single integrated circuit, or of a plurality of integrated circuits. The process in the processor 21 is executed according to a program stored in the processor 21 or storage medium 22. The storage medium 22 stores a processing program for use in the processor 21, as well as parameters and tables for use in arithmetic processing in the processor 21. The processor 21 includes an impedance detector 23, a determination section 25 and an output controller 26. The impedance detector 23, determination section 25 and output controller 26 function as parts of the processor 21, and execute some of the processes executed by the processor 21.

In the end effector 7 of the energy treatment instrument 2, the first grasping piece 15 is provided with a first electrode 27, and the second grasping piece 16 is provided with a second electrode 28. The electrodes 27 and 28 are formed of an electrically conductive material. The control device 3 includes an electric power source 31, which may be a battery or an electric power receptacle, and an energy output source (first energy output source) 32. The energy output source 32 is electrically connected to the electrodes 27 and 28 via an electricity supply path (first electricity supply path) 33 that extends inside the cable 10. The energy output source 32 includes a converter circuit, an amplifier circuit, and the like, and converts the electric power supplied from the electric power source 31. The energy output source 32 outputs the converted electric energy (high-frequency electric power). The electric energy that is output from the energy output source 32 is supplied to the electrodes 27 and 28 through the electricity supply path 33. The output controller 26 of the processor 21 controls the driving of the energy output source 32, and controls the output of the electric energy from the energy output source 32. In this manner, any of output electric power P, output current I and output voltage V of the energy output source 32 is adjusted, and the supply of the electric energy to the electrodes 27 and 28 is controlled.

The electric energy is supplied from the energy output source 32 to the electrodes 27 and 28 with a treatment target being grasped between the grasping pieces 15 and 16. A high-frequency current thereby flows between the electrodes 27 and 28 through the treatment target that is being grasped in contact with the electrodes 27 and 28. That is, the high-frequency current is supplied as treatment energy to the treatment target. Due to the high-frequency current flowing through the treatment target, heat is caused in the treatment target, and this heat denatures the treatment target. The treatment target, such as a blood vessel, is sealed (coagulated) by using the high-frequency current. As described above, with the electric energy supplied from the energy output source 32 to the electrodes 27 and 28 of the energy treatment instrument 2, the treatment energy (high-frequency current) is applied to the treatment target grasped between the grasping pieces 15 and 16. According to the present embodiment, the grasping pieces 15 and 16 function as an energy application section (energy applier) that applies the high-frequency current as treatment energy to the grasped treatment target (blood vessel).

The electricity supply path 33 is provided with a current detection circuit 35 and a voltage detection circuit 36. When the electric energy is being output from the energy output source 32, the current detection circuit 35 detects the output current I, and the voltage detection circuit 36 detects the output voltage V. The energy control device 3 is provided with an A/D converter 37. To this A/D converter 37, an analog signal relating to the current I detected by the current detection circuit 35, and an analog signal relating to the voltage V detected by the voltage detection circuit 36 are transmitted. The A/D converter 37 converts the analog signal relating to the current I and the analog signal relating to the voltage V to digital signals, and transmits the converted digital signals to the processor 21.

When the electric energy is being output from the energy output source 32, the processor 21 acquires information relating to the output current I and the output voltage V of the energy output source 32. The impedance detector 23 of the processor 21 detects the impedance of the electricity supply path 33 including the grasped treatment target (blood vessel) and the electrodes 27 and 28, based on the output current I and the output voltage V. In this manner, an impedance Z between the paired grasping pieces 15 and 16 (i.e. the impedance of the grasped treatment target) is detected.

As illustrated in FIG. 1, an operation button 18 is attached to the housing 5 to function as an energy operation input section. By pressing the operation button 18, an operation (signal) for outputting the electric energy from the energy output source 32 to the energy treatment instrument 2 is input to the control device 3. In place of the operation button 18 or in addition to the operation button 18, a foot switch or the like may be provided separately from the energy treatment instrument 2, as the energy operation input section. As illustrated in FIG. 2, the processor 21 detects the presence or absence of input of an operation from the energy operation input section such as the operation button 18. Based on the input of the operation by the operation button 18, the output controller 26 of the processor 21 controls the output of the electric energy from the energy output source 32.

As illustrated in FIGS. 1 and 2, the treatment system 1 includes a rigid endoscope (endoscope) 60 as an observation element (observation device). The rigid endoscope 60 has a longitudinal axis C'. In the rigid endoscope 60, one side of the direction along the longitudinal axis C' is a distal side (arrow C'1 side), and a side opposite to the distal side is a proximal side (arrow C'2 side). The rigid endoscope 60 includes an insertion section 61 extending along the longitudinal axis C', and a hand-held section 62 that can be hand-held and is provided on the proximal side of the insertion section 61. The treatment system 1 further includes an image processing device 65, and a display device 67 such as a monitor. One end of a universal cord 66 is connected to the hand-held section 62 of the rigid endoscope 60. The other end of the universal cord 66 is detachably connected to the image processing device 65. The image processing device 65 is electrically connected to the display device 67.

An imaging element 71 such as a CCD is provided in a distal portion of the insertion section 61 of the rigid endoscope 60. The imaging element 71 takes images of a subject. For example, when the blood vessel (treatment target) is being grasped between the grasping pieces 15 and 16, images of the grasped blood vessel, the grasping pieces 15 and 16 (end effector 7), and the like are taken, as a subject, by the imaging element 71. Here, the imaging element 71 may perform stereoscopic imaging. The imaging element 71 may continuously perform the imaging of the subject over time. The grasped blood vessel is observed with the rigid endoscope 60 in the above manner.

The image processing device 65 includes a processor (image processing section) 72 that executes the image processing or the like, and a storage medium 73. The processor 72 is formed of an integrated circuit including a CPU, ASIC, FPGA or the like. The processor 72 may be formed of a single integrated circuit, or of a plurality of integrated circuits. The process at the processor 72 is executed according to programs stored in the processor 72 or the storage medium 73. The storage medium 73 stores processing programs for use in the processor 72, as well as parameters and tables for use in the arithmetic processing in the processor 72. The processor 72 can communicate with (can exchange information with) the processor 21 of the control device 3 in a wired or wireless manner.

When an image of the subject is taken by the imaging element 71, an imaging signal is transmitted to the processor 72. The processor 72 thereby generates an observation image of the subject such as the grasped blood vessel. If the imaging element 71 executes stereoscopic imaging, the processor 72 generates a three-dimension image as the observation image of the subject. When the images of the subject are continuously taken over time, the processor 72 generates the observation images continuously over time. The observation images generated by the processor 72 are displayed on the display device 67. In an example, the processor 72 detects the angular position of the imaging element 71 (i.e. the attitude of the imaging element 71) around the longitudinal axis C' of the insertion section 61, using a gravity sensor (not shown) arranged in the rigid endoscope 60. Based on this detection result of the angular position or the like, the processor 72 generates an observation image in a manner that the upper side of the observation image corresponds to the upper side of the vertical direction. Here, the processor 72 may execute the processing similar to the image generating process based on the image orientation, which is one of the tabs of EXIF. The processor 72 may automatically rotate the image of the subject taken by the imaging element 71 to bring the upper side of the observation image to correspond to the upper side in the vertical direction.

Furthermore, by executing the image processing, the processor 72 acquires information regarding the subject from the generated observation image. For example, the processor 72 may determine the position of the grasped blood vessel in the observation image based on the brightness, colors, and the like of the pixels that constitute the observation image. Furthermore, the processor 72 detects a change in the position of the grasped blood vessel from the position immediately before, and creates an optical flow, which is a motion vector of the grasped blood vessel in the observation image. If the grasped blood vessel is not moved from the position immediately before in the observation image, the optical flow of the grasped blood vessel is a zero vector. The image data of the observation image generated by the processor 72 is transmitted to the processor 21 of the control device 3. In addition, the result of the image processing at the processor 72, such as the position of the grasped blood vessel in the observation image and the optical flow of the grasped blood vessel, is also transmitted to the processor 21 of the control device 3.

The determination section 25 of the processor 21 determines whether the grasped blood vessel is moved in a specific direction (to the upper side, for example) in the observation image, based on the image data of the generated observation image and the result of the image processing obtained by the processor 72. The determination section 25 of the processor 21 further determines, based on the determination result regarding the movement of the grasped blood vessel in the observation image, whether there is tension exerted on the grasped blood vessel, or in other words, whether the grasped blood vessel is being pulled between the grasping pieces 15 and 16. Based on the determination result regarding the tension on the grasped blood vessel, the output controller 26 of the processor 21 controls the output of the electric energy from the energy output source 32. In accordance with the output state of the electric energy from the energy output source 32, the actuation state of the energy treatment instrument 2 is switched between a first mode (first actuation mode) and a second mode (second actuation mode). According to the present embodiment, the state of the treatment energy (high-frequency current) applied from the energy application section (grasping pieces 15 and 16) to the grasped treatment target differs between the first mode and the second mode.

In one example, an ultrasonic transducer 46 may be provided in the energy treatment instrument 2 (inside the housing 5). If this is the case, a rod member is connected to the distal side of the ultrasonic transducer 46, and one of the grasping pieces 15 and 16 (e.g., the first grasping piece 15) is constituted by a projecting portion of this rod member that projects from the sheath 6 toward the distal side. In this example, in addition to the energy output source 32, an energy output source (second energy output source) 47 is provided in the control device 3. The energy output source 47 is electrically connected to the ultrasonic transducer 46 via an electricity supply path (second electricity supply path) 48 extending inside the cable 10. The energy output source 47 may be formed integrally with the energy output source 32, or may be formed separately from the energy output source 32.

In this example, the energy output source 47 includes a converter circuit, an amplifier circuit, and the like, and converts electric power from the electric power source 31. In addition, the energy output source 47 outputs the converted electric energy (AC electric power). The electric energy that is output from the energy output source 47 is supplied to the ultrasonic transducer 46 through the electricity supply path 48. The output controller 26 of the processor 21 controls the driving of the energy output source 47, and controls the output of the electric energy from the energy output source 47.

In the present example, the electric energy (AC electric power) that is output from the energy output source 47 is supplied to the ultrasonic transducer 46 so that ultrasonic vibrations can be generated in the ultrasonic transducer 46. The generated ultrasonic vibrations are transmitted from the proximal side toward the distal side in the rod member (vibration transmitting member) so that the rod member including one of the grasping pieces 15 and 16 (e.g., first grasping piece 15) vibrates. By the rod member vibrating in the state of the treatment target being grasped between the grasping pieces 15 and 16, the ultrasonic vibrations are applied to the treatment target as treatment energy. At this time, frictional heat is generated from the vibrations, and the treatment target such as the blood vessel can be incised, while being sealed (coagulated), by use of the frictional heat.

In another example, a heater (not shown) may be provided, in place of the ultrasonic transducer 46, in the end effector 7 (at least one of the grasping pieces 15 and 16). If this is the case, the electric energy (DC electric power or AC electric power) that is output from the energy output source (47) is supplied to the heater through the electricity supply path (48). Heat is thereby generated by the heater, and the treatment target such as the blood vessel can be incised, while being sealed (coagulated), by use of the heat generated by the heater. When the ultrasonic vibration and the heat of the heater are applied as treatment energy to the grasped treatment target (blood vessel), at least one of the grasping pieces 15 and 16 still functions as the energy application section that applies the treatment energy to the treatment target.

Next, the function and advantageous effects of the present embodiment will be discussed. When a treatment is performed by using the treatment system 1, a surgeon holds the housing 5 of the energy treatment instrument 2, and inserts the end effector 7 into a body cavity such as an abdominal cavity. With the blood vessel (treatment target) being placed between the grasping pieces 15 and 16, the handle 12 is closed with respect to the grip 11 so that the grasping pieces 15 and 16 can be closed relative to each other. In this manner, the blood vessel is grasped between the grasping pieces 15 and 16. At the same time, the insertion section 61 of the rigid endoscope 60 is also inserted into the body cavity, and the imaging element 71 continuously takes images of the grasped blood vessel and grasping pieces 15 and 16 as a subject, over time. The grasped blood vessel is observed in this manner. Then, high-frequency current may be applied as treatment energy to the blood vessel so as to conduct a sealing treatment of the grasped blood vessel.

Figure 3:
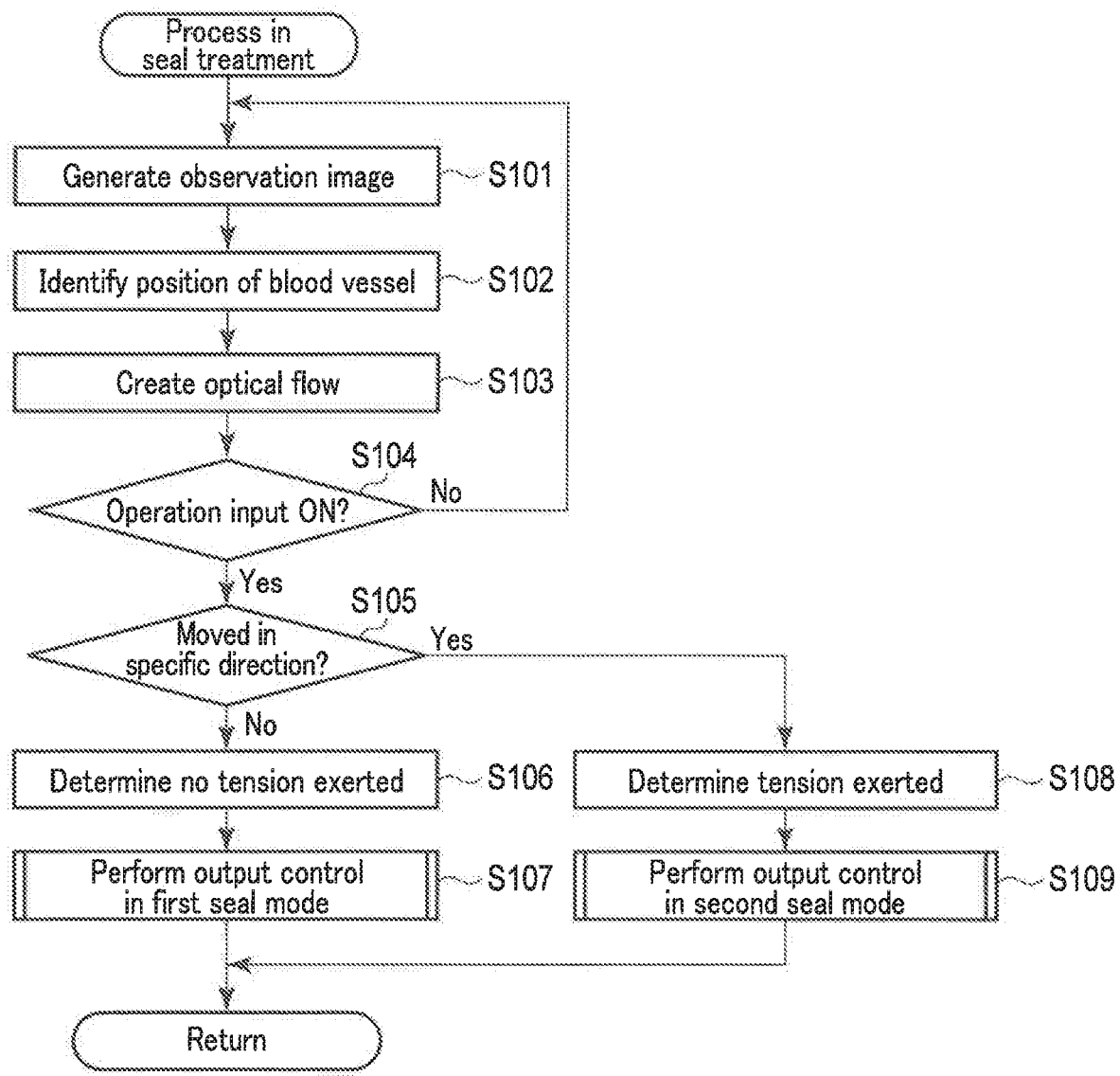
FIG. 3 is a flowchart illustrating a process in a processor in a seal treatment of a blood vessel using the treatment system according to the first embodiment.

FIG. 3 is a flowchart of a process executed by the processors 21 and 72 in a seal treatment of a blood vessel using the treatment system 1 of the present embodiment. As illustrated in FIG. 3, when performing the seal treatment of the blood vessel, the processor 72 generates an observation image, based on a subject image taken by the imaging element 71 (step S101). For instance, the observation image may be generated in a manner that the upper side of the observation image corresponds to the upper side in the vertical direction. In another example, the surgeon may rotate the rigid endoscope 60 around the longitudinal axis C', thereby adjusting the angular position of the imaging element 71 around the longitudinal axis C' so as to bring the upper side of the observation image to correspond to the upper side in the vertical direction. The generated observation image is displayed on the display device 67. The processor 72 identifies the position of the grasped blood vessel in the observation image, based on the luminance, colors, or the like of the pixels which constitute the observation image (step S102). The display screen of the display device 67 may be a touch panel, and the operation of indicating the position of the grasped blood vessel in the observation image may be input, for example, by the surgeon on the touch panel of the display device 67. If this is the case, the processor 72 identifies the position of the grasped blood vessel in the observation image, based on the operation input on the touch panel. The processor 72 creates an optical flow, which is the motion vector of the grasped blood vessel in the observation image (step S103).

The processor 21 of the control device 3 determines whether an operation input has been made using the operation button (energy operation input section) 18 (i.e., whether the operation input is ON or OFF) (step S104). If no operation input is made (No at step S104), the process returns to step S101, where the processes of step S101 and thereafter are executed. In this manner, the generation of an observation image and the creation of an optical flow of the grasped blood vessel in the observation image are repeated. When the operation input is made (Yes at step S104), the determination section 25 of the processor 21 determines, based on the optical flow of the grasped blood vessel, whether the grasped blood vessel is moved in a specific direction (e.g. to the upper side) in the observation image (step S105). Here, the determination is made based on the observation image and optical flow of the grasped blood vessel obtained at a time point when the operation input was switched from OFF to ON, or at a time point close to this time point. The optical flow of the grasped blood vessel may be displayed on the display device 67.

If it is determined that the grasped blood vessel is not moved (i.e., the optical flow being a zero vector), or that the grasped blood vessel is moved in a direction (e.g., to the lower side in observation image) that is different from a specific direction (i.e., the direction of the optical flow being different from a specific direction) (No at step S105), the determination section 25 of the processor 21 determines that there is no tension exerted on the grasped blood vessel (treatment target) (step S106). That is, it is determined that the grasped blood vessel is not pulled. Thereafter, the output controller 26 of the processor 21 executes the output control of the electric energy from the energy output source 32 in a first seal mode (step S107).

If it is determined that the grasped blood vessel is moved in a specific direction (e.g. to the upper side) in the observation image (i.e., the direction of the optical flow corresponding to the specific direction) (Yes at step S105), the determination section 25 of the processor 21 determines that there is tension exerted on the grasped blood vessel (treatment target) (step S108). That is, it is determined that the grasped blood vessel is being pulled. Then, the output controller 26 executes the output control of the electric energy from the energy output source 32 in a second seal mode that is different from the first seal mode (step S109). When an operation is input using the operation button (energy operation input section) 18 and the treatment energy is being applied to the grasped blood vessel, the processor 72 still generates an observation image, based on the subject image taken by the imaging element 71.

Figure 4:
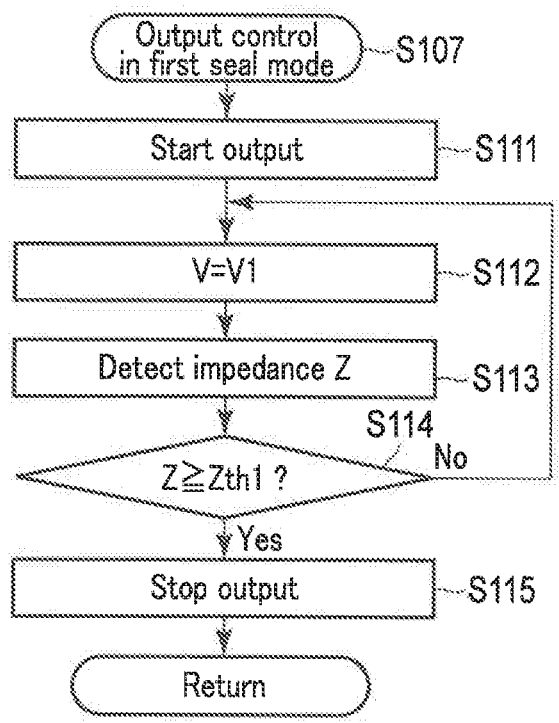
FIG. 4 is a flowchart illustrating a process in output control in a first seal mode of the processor according to the first embodiment.

FIG. 4 is a flowchart indicating the process of the processor 21 in the output control in the first seal mode. As illustrated in FIG. 4, the processor 21 starts the output of the electric energy (high-frequency electric power) from the energy output source (first energy output source) 32 in the first seal mode of the output control (step S111). In this manner, the electric energy is supplied to the electrodes 27 and 28, and a high-frequency current flows through the grasped blood vessel, thereby sealing the blood vessel.

When a certain period of time has elapsed from the start of the output of the electric energy from the energy output source 32, the output controller 26 executes a constant voltage control to keep the output voltage V from the energy output source 32 constant at a first voltage V1 over time (step S112). Furthermore, when the output of the electric energy from the energy output source 32 is started, the impedance detector 23 of the processor 21 detects the impedance Z between the grasping pieces 15 and 16 (i.e. the impedance of the grasped treatment target), based on the detection result of the output current I obtained by the current detection circuit 35 and the detection result of the output voltage V obtained by the voltage detection circuit 36 (step S113). Then, the processor 21 determines whether a detected impedance Z is greater than or equal to an impedance threshold (first impedance threshold) Zth1 (step S114). The impedance threshold Zth1 may be set, for example, by the surgeon, or may be stored in the storage medium 22.

If the impedance Z is lower than the impedance threshold Zth1 (No at step S114), the process returns to step S112, and the processes of step S112 and thereafter are executed. If the impedance Z is greater than or equal to the impedance threshold Zth1 (Yes at step S114), the output controller 26 stops the output of the electric energy (high-frequency electric power) from the energy output source 32 (step S115). Thus, the supply of the electric energy to the electrodes 27 and 28 is stopped. The processor 21 executes the output control of the electric energy from the energy output source 32 in the first seal mode, and thereby the energy treatment instrument 2 is actuated in the first mode in which the grasped treatment target is coagulated (the blood vessel is sealed).

In the second seal mode of the output control, the processor 21 executes the processes of steps S111 and S113 to S115, similarly to the first seal mode of the output control. However, in the second seal mode, when a certain period of time has elapsed from the start of the output of the electric energy from the energy output source 32, the output controller 26 executes a constant voltage control for keeping the output voltage V from the energy output source 32 constant over time at a second voltage value V2, which is lower than the first voltage V1. In the second seal mode, because the constant voltage control is executed at the second voltage value V2 that is lower than the first voltage V1, the electric energy that is output from the energy output source 32 is lower in the second seal mode than in the first seal mode. In other words, the output controller 26 of the processor 21 reduces the electric energy to be output from the energy output source 32 in the second seal mode, in comparison to the first seal mode. The processor 21 executes the output control of the electric energy from the energy output source 32 in the second seal mode so that the energy treatment instrument 2 coagulates the grasped treatment target (seals the blood vessel), and is actuated in the second mode which is different from the first mode. As described above, in the present embodiment, the processor 21 controls the output of the electric energy from the energy output source 32, based on the determination result of the tension, thereby switching the actuation state of the energy treatment instrument 2 between the first mode (first actuation mode) and the second mode (second actuation mode). The output state of the electric energy from the energy output source 32 differs between the first seal mode and the second seal mode. Thus, in the energy treatment instrument 2, the state of the treatment energy (high-frequency current) applied from the energy application section (grasping pieces 15 and 16) to the grasped treatment target differs between the first mode and the second mode.

As long as the electric energy to be output from the energy output source 32 becomes smaller in the second seal mode than in the first seal mode, the output control that is not the constant voltage control may be executed in the first seal mode and in the second seal mode. In one example, in the first seal mode, the output controller 26 may execute a constant electric power control to keep the output electric power P from the energy output source 32 constant over time at a first electric power P1. In the second seal mode, the output controller 26 executes a constant electric power control to keep the output electric power P from the energy output source 32 constant over time at a second electric power P2 that is lower than the first electric power P1. In another example, both the constant voltage control for keeping the output voltage V constant over time at the first voltage V1 and the constant electric power control for keeping the output electric power P constant over time at the first electric power P1 may be executed in the first seal mode, and switching is performed between the constant voltage control and the constant electric power control in accordance with the impedance Z. In the second seal mode, both the constant voltage control for keeping the output voltage V constant over time at the second voltage value V2 that is lower than the first voltage V1, and the constant electric power control for keeping the output electric power P constant over time at the second electric power P2 that is lower than the first electric power P1 may be executed, and switching is performed between the constant voltage control and the constant electric power control in accordance with the impedance Z. In any of the examples, the electric energy that is output from the energy output source 32 in the second seal mode is smaller than in the first seal mode.

According to the present embodiment, only the high-frequency current is applied as treatment energy to the blood vessel in each of the first seal mode and the second seal mode, and therefore the treatment energy other than the high-frequency current, such as ultrasonic vibrations and the heat of the heater, will not be applied to the blood vessel (treatment target). For instance, in the example in which the ultrasonic transducer 46 is provided in the energy treatment instrument 2, the processor 21 stops the output of the electric energy from the energy output source 47 to the ultrasonic transducer 46 in each of the first seal mode and the second seal mode. Thus, no electric energy is supplied to the ultrasonic transducer 46 in the first seal mode and second seal mode, and therefore no ultrasonic vibration will be generated by the ultrasonic transducer 46. Similarly, in the example in which a heater is provided in the energy treatment instrument 2, the processor 21 stops the output of the electric energy from the energy output source to the heater in each of the first seal mode and second seal mode. Thus, no electric energy is supplied to the heater in the first seal mode and second seal mode, and therefore no heat will be generated by the heater.

In one example, when the output control in the first seal mode or the output control in the second seal mode ends, no electric energy is supplied to the electrodes 27 and 28, the ultrasonic transducer 46, or the heater, and therefore no treatment energy, such as high-frequency current, ultrasonic vibrations, or the heat of the heater, will be applied to the treatment target. In another example, when the output control in the first seal mode or the output control in the second seal mode ends, the output control is automatically shifted to an incision mode. If this is the case, in the example in which the ultrasonic transducer 46 is provided in the energy treatment instrument 2, the processor 21 causes the energy output source 47 to output the electric energy to the ultrasonic transducer 46 at an incision level (high output level) in the incision mode. This causes the ultrasonic transducer 46 to produce ultrasonic vibrations and transmit the ultrasonic vibrations to one of the grasping pieces 15 and 16. The transmitted ultrasonic vibrations are applied as the treatment energy to the grasped blood vessel (treatment target), and the blood vessel is incised by frictional heat generated by the ultrasonic vibrations. Similarly, in the example in which the heater is provided in the energy treatment instrument 2, the processor 21 causes the energy output source to output the electric energy at the incision level (high output level) to the heater in the incision mode. The heater thereby generates heat. This heat of the heater is applied as the treatment energy to the grasped blood vessel, and the blood vessel is incised.

Figure 5:
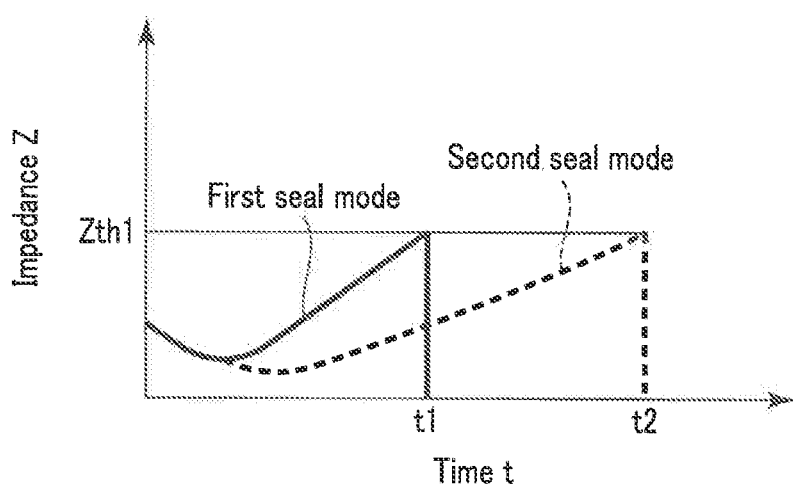
FIG. 5 is a schematic diagram illustrating an example of a variation of an impedance with time between a pair of grasping pieces, in a state in which the processor according to the first embodiment is executing output control in the first seal mode and in the second seal mode.

FIG. 5 is a diagram illustrating an example of a variation of the impedance Z with time between the paired grasping pieces 15 and 16 (i.e. the impedance of the grasped treatment target) in the state in which the processor 21 is executing the output control in the first seal mode and in the second seal mode. In FIG. 5, the ordinate axis indicates the impedance Z, and the abscissa axis indicates time t with reference to the start of the output of the electric energy from the energy output source 32. In FIG. 5, a solid line indicates a variation with time of the impedance Z in the first seal mode, and a broken line indicates a variation with time of the impedance Z in the second seal mode. As shown in FIG. 5, when the output of the electric energy from the energy output source 32 is started and the high-frequency current begins to flow through the blood vessel (treatment target), the impedance Z normally exhibits a behavior of decreasing with time for a certain length of time. After the impedance Z decreases with time to a certain level, the impedance Z normally exhibits a behavior of increasing with time in accordance with the rise in temperature of the treatment target due to the heat generated by the high-frequency current.

As described above, the electric energy that is output from the energy output source 32 in the second seal mode is lower than in the first seal mode according to the present embodiment. For this reason, in comparison with the first seal mode, the amount of heat generated per unit time due to the high-frequency current flowing in the blood vessel (treatment target) is smaller in the second seal mode. Accordingly, the rate of temperature rise of the treatment target (blood vessel) is lower, and the rate of increase of the impedance Z in the state in which the impedance Z increases with time is lower in the second seal mode than in the first seal mode. This means that the time length from the output start of the electric energy from the energy output source 32 to the time of the impedance Z reaching the impedance threshold $Z_{th1}$ is longer in the second seal mode than in the first seal mode.

In fact, in the example of FIG. 5, the impedance Z reaches the impedance threshold $Z_{th1}$ at time t1 in the first seal mode, whereas the impedance Z reaches the impedance threshold $Z_{th1}$ at time t2, which is later than time t1, in the second seal mode. As described above, in each of the first seal mode and second seal mode according to the present embodiment, the output of the electric energy from the energy output source 32 is stopped in accordance with the impedance Z reaching or exceeding the impedance threshold $Z_{th1}$. For this reason, the output time length of the electric energy from the energy output source 32 is longer in the second seal mode than in the first seal mode.

As described above, in comparison to the first seal mode, the output controller 26 (processor 21) reduces the electric energy output from the energy output source 32, and increases the output time length of the electric energy from the energy output source 32 in the second seal mode. This means that, in comparison to the first seal mode, the amount of heat generated per unit of time due to the high-frequency current in the blood vessel is smaller, and the time length of the high-frequency current being supplied to the blood vessel is longer in the second seal mode. That is, in the energy treatment instrument 2, the time length of the treatment energy (high-frequency current) being applied from the energy application section (grasping pieces 15 and 16) to the treatment target (blood vessel) is longer in the second mode (second actuation mode) than in the first mode (first actuation mode). The total amount of treatment energy (high-frequency current) applied to the treatment target in the first seal mode corresponds to, for example, the area defined by the impedance Z indicated by the solid line and time t in FIG. 5. The total amount of treatment energy (high-frequency current) applied to the treatment target in the second seal mode corresponds to, for example, the area defined by the impedance Z indicated by the broken line and time t in FIG. 5. In FIG. 5, the area on the lower side of the impedance Z in the second seal mode, defined by the broken line, is larger than the area on the lower side of the impedance Z in the first seal mode, defined by the solid line. The performance of sealing the blood vessel by the high-frequency current is therefore higher in the second seal mode than in the first seal mode.

Figure 6:
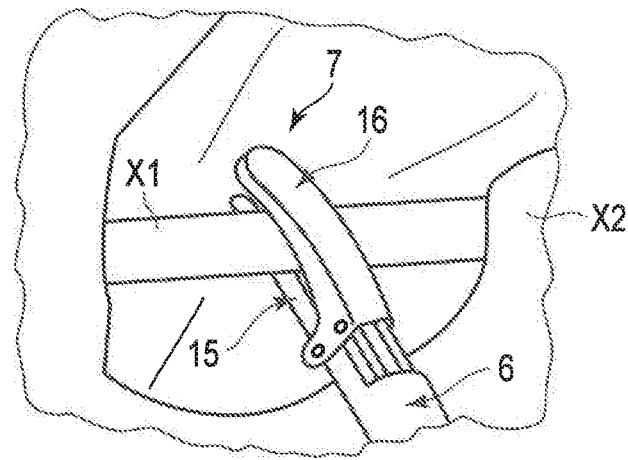
FIG. 6 is a schematic diagram illustrating an example of an observation image in which a blood vessel is grasped between the grasping pieces without being pulled, according to the first embodiment.
Figure 7:
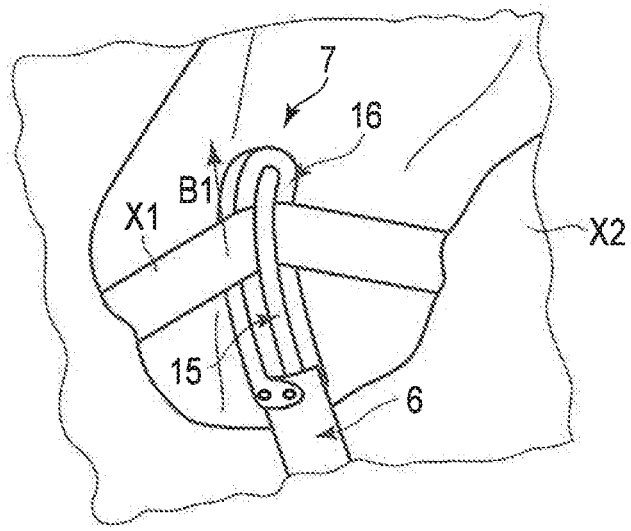
FIG. 7 is a schematic diagram illustrating an example of an observation image in which the blood vessel grasped between the grasping pieces is pulled to one side in a direction intersecting with an extending direction of the blood vessel according to the first embodiment.

Each of FIGS. 6 and 7 is a diagram illustrating an example of an observation image generated by the processor 72 in a state in which a blood vessel X1 is grasped between the grasping pieces 15 and 16. When grasping the blood vessel X1, the blood vessel X1 may be grasped, as illustrated in FIG. 6, without being pulled in a direction intersecting (substantially perpendicular to) the extending direction of the blood vessel X1. Alternatively, the blood vessel X1 may be grasped as illustrated in FIG. 7, in which it is pulled to one side in the direction intersecting the extending direction of the blood vessel X1. As discussed above, when the blood vessel X1 is pulled, tension is exerted on the portion of the blood vessel X1 that is being pulled. For this reason, in the grasping piece (15 or 16) which is located on the side opposite to the side of the blood vessel X1 being pulled with respect to the blood vessel, the load to the opening side of this grasping piece (15 or 16) is increased. When the load on the opening side in one of the grasping pieces (15 or 16) increases, the treatment of sealing a grasped blood vessel X1 by using the treatment energy such as a high-frequency current may be affected. Thus, there is a possibility that the performance of sealing the blood vessel X1, as represented by a pressure resistance value of the sealed blood vessel X1, may be affected.

In the treatment of sealing the blood vessel X1, the end effector 7 of the energy treatment instrument 2 and the insertion section 61 of the rigid endoscope 60 are inserted vertically from above into a body cavity such as abdominal cavity and pleural cavity of a patient lying on his/her back. Thereafter, the blood vessel X1 of an internal organ X2 such as the liver or lungs is sealed in the body cavity. For this reason, the internal organ X2 is present in the direction (e.g., on the vertical lower side) other than the upper side of the vertical direction with respect to the grasped blood vessel X1, and if the grasped blood vessel X1 is moved in a direction different from the upper side of the vertical direction in the treatment, the blood vessel X1 will interfere with the internal organ X2 or the like. Thus, the grasped blood vessel X1 can be pulled only toward the upper side of the vertical direction in the treatment, and the grasped blood vessel X1 cannot be pulled in any direction different from the upper side of the vertical direction. Thus, the upper side (specific direction) of the observation image is brought to correspond to the upper side in the vertical direction, and whether the grasped blood vessel X1 is moved in a specific direction (e.g., toward the upper side) in the observation image is determined based on the optical flow. In this manner, whether or not there is tension exerted onto the grasped blood vessel X1 can be suitably determined. In the observation image in FIG. 6, the optical flow of the grasped blood vessel X1 is a zero vector, while in the observation image in FIG. 7, the optical flow of the blood vessel X1 is vector B1 having a specific direction (e.g., upper side).

As discussed above, the processor 21 according to the present embodiment determines whether the grasped blood vessel is moved to a specific direction (upper side) in the observation image, and whether there is tension exerted onto the grasped blood vessel. When it is determined that there is no tension exerted on the blood vessel (i.e. that the blood vessel is not moved in a specific direction in the observation image), the output control is executed in the first seal mode. When it is determined that there is tension exerted on the blood vessel (i.e. that the blood vessel is moved in a specific direction in the observation image), the output control is executed in the second seal mode. Thus, in comparison to the case in which it is determined that there is no tension exerted on the grasped blood vessel, the electric energy that is output from the energy output source 32 is smaller and the output time length of the electric energy from the energy output source 32 is longer when it is determined that there is tension exerted on the grasped blood vessel. That is, in the energy treatment instrument 2, the time length of the treatment energy (high-frequency current) supplied from the energy application section (grasping pieces 15 and 16) to the treatment target (blood vessel) is longer in the second mode (second actuation mode) when it is determined that there is tension exerted onto the grasped blood vessel than in the first mode (first actuation mode) when it is determined that there is no tension exerted. According to the present embodiment, the determination of whether there is tension exerted on the grasped blood vessel X1 can be suitably made, as discussed above. Thus, when tension is exerted on the grasped blood vessel, the treatment is performed in the second seal mode, in which the performance of sealing the blood vessel using the high-frequency current by the energy treatment instrument 2 of the treatment system 1 is higher than in the first seal mode. Thus, the blood vessel can be sealed to the same degree as when tension is not exerted on the grasped blood vessel. By using the energy treatment instrument 2 of the treatment system 1, the sealing performance of the blood vessel, as represented for example by a pressure resistance value of the sealed blood vessel (resistance of the blood flow to the sealed region), can be easily maintained even when tension is exerted on the blood vessel.

As described above, even when there is tension exerted onto the grasped blood vessel X1, the grasped blood vessel can be suitably sealed by increasing the performance of sealing the blood vessel using the high-frequency current according to the present embodiment. That is, even when the blood vessel X1 is grasped while being pulled to one side in the direction intersecting the extending direction of the blood vessel X1, the blood vessel X1 can be suitably sealed using the treatment energy such as a high-frequency current, and a suitable treatment performance (sealing performance) can be achieved.

Modifications of First Embodiment

According to a first modification of the first embodiment, the process performed by the processor 21 in the second seal mode of the output control differs from the process in the first embodiment. For the first seal mode of the output control in this modification, the processor 21 executes the same process as in the first embodiment (see FIG. 4). For the second seal mode of the output control also, the processor 21 executes the process of step S111 to S113 in the same manner as in the first seal mode of the output control. In the second seal mode, however, the processor 21 determines whether the detected impedance Z is greater than or equal to an impedance threshold (second impedance threshold) Zth2, instead of executing the process of step S114. Here, the impedance threshold Zth2 is greater than the impedance threshold (first impedance threshold) Zth1. The impedance threshold Zth2 may be set, for example, by the surgeon, or may be stored in the storage medium 22.

If the impedance Z is smaller than the impedance threshold Zth2, the process returns to step S112, where the processes of step S112 and thereafter are executed. If the impedance Z is greater than or equal to the impedance threshold Zth2, the output controller 26 stops the output of the electric energy (high-frequency electric power) from the energy output source 32. Accordingly, in the second seal mode of the present modification, the output of the electric energy from the energy output source 32 is stopped in response to the impedance Z having reached or exceeded the impedance threshold (second impedance threshold) Zth2, which is greater than the impedance threshold (first impedance threshold) Zth1. The processor 21 controls the output of the electric energy from the energy output source 32, based on the determination result of the tension, and thereby switches the actuation state of the energy treatment instrument 2 between the first mode (first actuation mode) and the second mode (second actuation mode) in this modification. Furthermore, in this modification also, the state of the electric energy output from the energy output source 32 is different between the first seal mode and the second seal mode. Thus, in the energy treatment instrument 2, the state of the treatment energy (high-frequency current) applied from the energy application section (grasping pieces 15 and 16) to the grasped treatment target differs between the first mode and the second mode.

Figure 8:
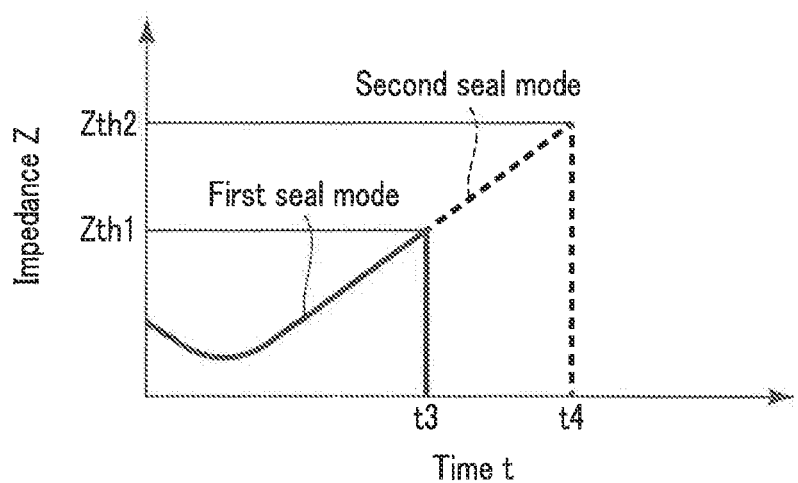
FIG. 8 is a schematic diagram illustrating an example of a variation of an impedance with time between a pair of grasping pieces in a state in which the processor according to the first modification of the first embodiment is executing output control in the first seal mode and in the second seal mode.

FIG. 8 is a diagram illustrating an example of a variation of the impedance Z with time between the paired grasping pieces 15 and 16 in the state in which the processor 21 of this modification is executing the output control in the first seal mode and in the second seal mode. In FIG. 8, the ordinate axis indicates the impedance Z, and the abscissa axis indicates time t with reference to the start of the output of the electric energy from the energy output source 32. Furthermore, in FIG. 8, a solid line indicates a variation with time of the impedance Z in the first seal mode, and a broken line indicates a variation with time of the impedance Z in the second seal mode.

As described above, in the present modification, the output of the electric energy from the energy output source 32 is stopped in response to the impedance Z having reached or exceeded the impedance threshold Zth1 in the first seal mode. On the other hand, in the second seal mode, the output of the electric energy from the energy output source 32 is stopped in response to the impedance Z having reached or exceeded the impedance threshold Zth2. The impedance threshold Zth2 is greater than the impedance threshold Zth1. Thus, the output time length of the electric energy from the energy output source 32 is longer in the second seal mode than in the first seal mode. In fact, in the example of FIG. 8, the output of the electric energy is stopped at time t3 in the first seal mode, whereas the output of the electric energy is stopped at time t4, which is later than time t3 in the second seal mode.

As described above, in the present modification, the output controller 26 (processor 21) sets the impedance threshold (Zth2), which serves as the reference for stopping the output, to be larger and the output time length of the electric energy from the energy output source 32 to be longer in the second seal mode than in the first seal mode. That is, in the energy treatment instrument 2 of the present modification, the time length of the treatment energy (high-frequency current) applied from the energy application section (grasping pieces 15 and 16) to the treatment target (blood vessel) is longer in the second mode (second actuation mode) in which it is determined that there is tension exerted onto the treatment target, than in the first mode (first actuation mode) in which it is determined that there is no tension exerted onto the grasped treatment target. Thus, in comparison to the first seal mode, the time length during which the high-frequency current is applied to the blood vessel is longer, and the total amount of treatment energy (high-frequency current) applied to the blood vessel is larger in the second seal mode, and the performance of sealing the blood vessel by the high-frequency current is thereby enhanced. Accordingly, when tension is exerted onto the grasped blood vessel, the treatment is performed in the second seal mode, in which the performance of the energy treatment instrument 2 of the treatment system 1 sealing the blood vessel by use of the high-frequency current is higher than the first seal mode. Thus, the blood vessel can be sealed to substantially the same degree as when no tension is exerted to the grasped blood vessel. By using the energy treatment instrument 2 of the treatment system 1, the blood vessel sealing performance as represented, for example, by a pressure resistance value of the sealed blood vessel (resistance to the blood flow to the sealed region) can be easily maintained even when there is tension exerted on the grasped blood vessel.

As one modification, the first embodiment and the first modification may be combined. If this is the case, the processor 21 reduces the electric energy output from the energy output source 32, and sets the impedance threshold (Zth2), which serves as the reference for stopping the output, to be larger in the second seal mode, in comparison to the first seal mode. The state of the electric energy output from the energy output source 32 differs between the first seal mode and second seal mode in this modification. Thus, in the energy treatment instrument 2, the state of the treatment energy (high-frequency current) applied from the energy application section (grasping pieces 15 and 16) to the grasped treatment target differs between the first mode and the second mode.

Figure 9:
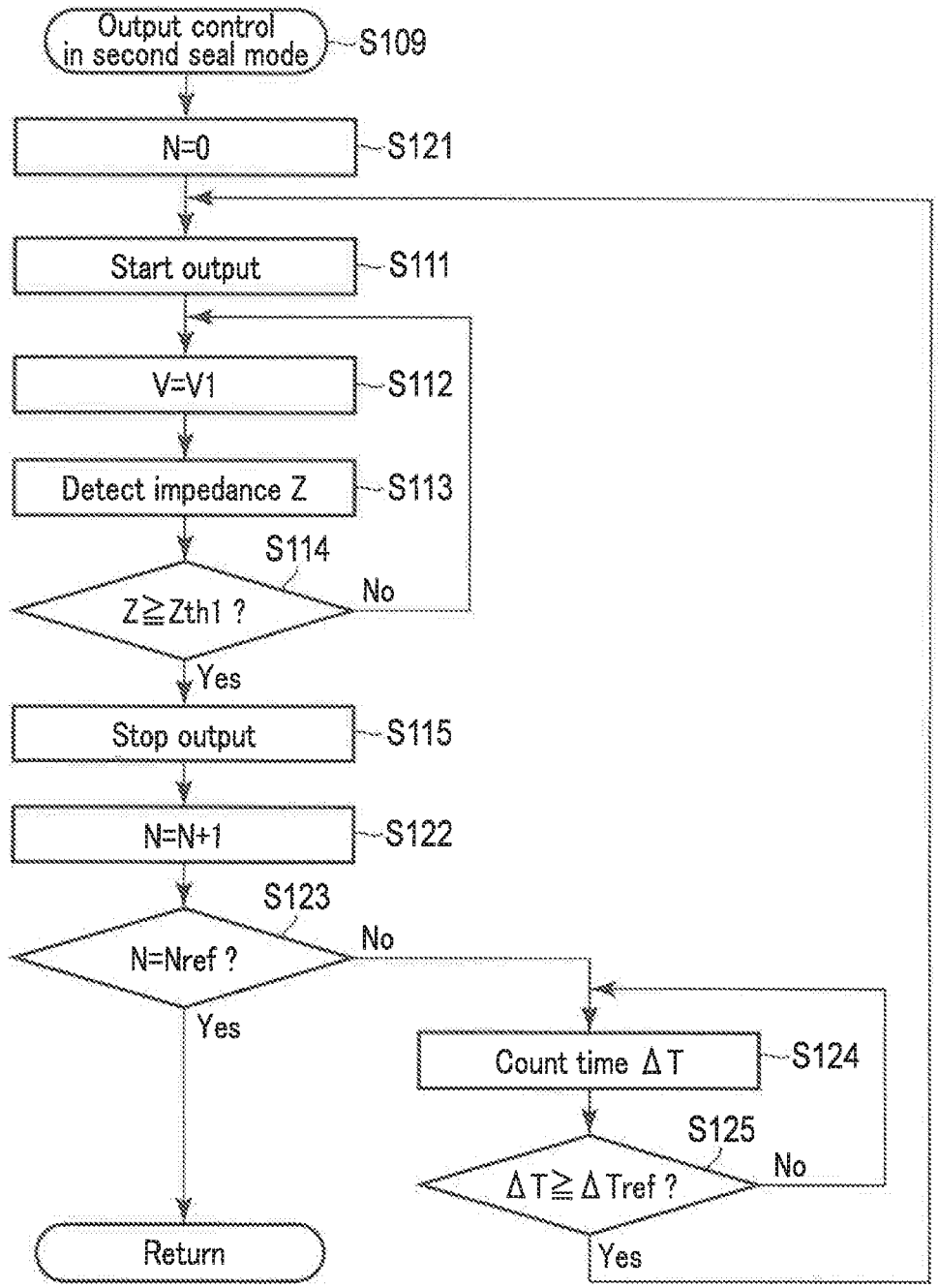
FIG. 9 is a flowchart illustrating a process in the second seal mode of the output control executed by the processor according to the second modification of the first embodiment.

Furthermore, in a second modification of the first embodiment, the processor 21 executes a process illustrated in FIG. 9 in the second seal mode of the output control. In the first seal mode of the output control in the present modification, the processor 21 executes the same process as in the first embodiment (see FIG. 4). In this modification, the number of outputs N is defined as a parameter for the electric energy from the energy output source 32 in the second seal mode of the output control. In the second seal mode of the output control, the processor 21 sets 0 as a default value for the number of outputs N (step S121). In the same manner as in the first seal mode of the output control, the processor 21 executes the processes of steps. S111 to S115.

When the output of the electric energy from the energy output source 32 is stopped by the process at step S115, the processor 21 increments the number of outputs N by 1 (step S122). Then, the processor 21 determines whether the incremented number of outputs N is equal to a reference number of times Nref (step S123). The reference number of times Nref is any natural number greater than or equal to 2, which may be set, for example, by the surgeon, or may be stored in the storage medium 22. If the number of outputs N is equal to the reference number of times Nref, or in other words, if the number of outputs N has reached the reference number of times Nref (Yes at step S123), the processor 21 terminates the output control in the second seal mode. In this manner, the state in which the output of the electric energy from the energy output source 32 is stopped is maintained.

Here, the time elapsed from the latest time point (time point 0) of the time points at which the output of the electric energy from the energy output source 32 is stopped by the process at step S115 is defined as $\Delta T$. If the number of outputs N is not equal to the reference number of times Nref, or in other words, if the output number of times N has not reached the reference number of times Nref (No at step S123), the processor 21 counts the time $\Delta T$ (step S124). Then, the processor 21 determines whether the counted time $\Delta T$ is greater than or equal to a reference time $\Delta Tref$ (step S125). The reference time $\Delta Tref$ may be, for example, 10 msec, which may be set, for example, by the surgeon, or may be stored in the storage medium 22.

If the time $\Delta T$ is shorter than the reference time $\Delta Tref$ (No at step S125), the process returns to step S124, and the processes of step S124 and thereafter are executed. Specifically, the state in which the output of the electric energy from the energy output source 32 is stopped is maintained, and the time $\Delta T$ continues to be counted. If the time $\Delta T$ is the reference time $\Delta Tref$ or greater (Yes at step S125), the process returns to step S111, and the processes of step S111 and thereafter are executed. In other words, the output of the electric energy from the energy output source 32 is resumed.

With the above process, in the second seal mode of the output control, the output controller 26 of the processor 21 stops the output of the electric energy after starting the output of the electric energy from the energy output source 32. Furthermore, after suspending the output of the electric energy from the energy output source 32, the output controller 26 resumes the output of the electric energy. That is, in the second seal mode, when the reference time $\Delta Tref$ has passed after the time point of suspending the output of the electric energy from the energy output source 32, the electric energy is output once again from the energy output source 32. During the output control in the second seal mode, the processor 21 causes the energy output source 32 to intermittently output the electric energy for the reference number of times Nref (multiple times). The processor 21 controls, in the present modification, the output of the electric energy from the energy output source 32, based on the determination result of the tension, and thereby switches the actuation state of the energy treatment instrument 2 between the first mode (first actuation mode) and the second mode (second actuation mode). The output state of the electric energy from the energy output source 32 differs between the first seal mode and second seal mode in this modification, and therefore the application state of the treatment energy (high-frequency current) from the energy application section (grasping pieces 15 and 16) to the grasped treatment target in the energy treatment instrument 2 differs between the first mode and the second mode.

Figure 10:
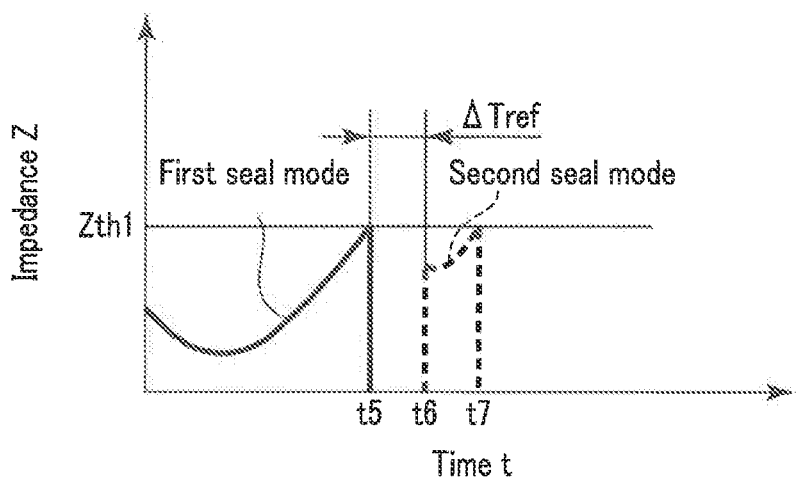
FIG. 10 is a schematic diagram illustrating an example of a variation of an impedance with time between the pair of grasping pieces, in a state in which the processor according to the second modification of the first embodiment is executing the output control in the first seal mode and in the second seal mode.

FIG. 10 is a diagram illustrating an example of a variation of the impedance Z with time between the paired grasping pieces 15 and 16 in the state in which the processor 21 of this modification is executing the output control in the first seal mode and in the second seal mode. In FIG. 10, the ordinate axis indicates the impedance Z, and the abscissa axis indicates time t with reference to the start of the output of the electric energy from the energy output source 32. Furthermore, in FIG. 10, a solid line indicates a variation with time of the impedance Z in the first seal mode, and a broken line indicates a variation with time of the impedance Z in the second seal mode. In the example shown in FIG. 10, the output of the electric energy from the energy output source 32 is stopped at time t5, in response to the impedance Z having reached the impedance threshold Zth1, in each of the first seal mode and second seal mode.

As described above, in the present modification, the electric energy is intermittently output from the energy output source 32 for multiple times (reference number of times Nref) in the second seal mode. In the second seal mode in the example shown in FIG. 10, the output of the electric energy from the energy output source 32 is resumed at time t6 when the reference time $\Delta Tref$ has elapsed from time t5 at which the output was stopped. Here, the impedance Z is smaller than the impedance threshold Zth1. At time t7 after the time t6 (at which the output of the electric energy was resumed), in response to the impedance Z having reached the impedance threshold Zth1, the output of the electric energy from the energy output source 32 is stopped once again. In the example of FIG. 10, the reference number of times Nref is 2.

As described above, in the present modification, the output controller 26 (processor 21) resumes the output of the electric energy after suspending the output in the second seal mode. The output time length of the electric energy from the energy output source 32 therefore becomes longer in the second seal mode than in the first seal mode, as a result of which the time length of the high-frequency current being applied to the blood vessel becomes longer in the second seal mode than in the first seal mode. That is, in the energy treatment instrument 2 of the present modification, the time length of the treatment energy (high-frequency current) being applied from the energy application section (grasping pieces 15 and 16) to the treatment target (blood vessel) is longer in the second mode (second actuation mode), in which the determination is that there is tension exerted onto the grasped treatment target, than in the first mode (first actuation mode), in which the determination is that there is no tension exerted onto the grasped treatment target. For this reason, the performance of sealing the blood vessel by the high-frequency current is higher in the second seal mode than in the first seal mode. Accordingly, when there is tension exerted onto the grasped blood vessel, the treatment is performed in the second seal mode, in which the performance of sealing the blood vessel using the high-frequency current of the energy treatment instrument 2 of the treatment system 1 is higher than in the first seal mode. Thus, the blood vessel can be sealed to substantially the same degree as when no tension is exerted to the grasped blood vessel. By using the energy treatment instrument 2 of the treatment system 1, the performance of sealing the blood vessel, as represented, for example, by the pressure resistance value of the sealed blood vessel (resistance of the blood flow to the sealed region), can be readily maintained even when tension is exerted on the blood vessel.

Figure 11:
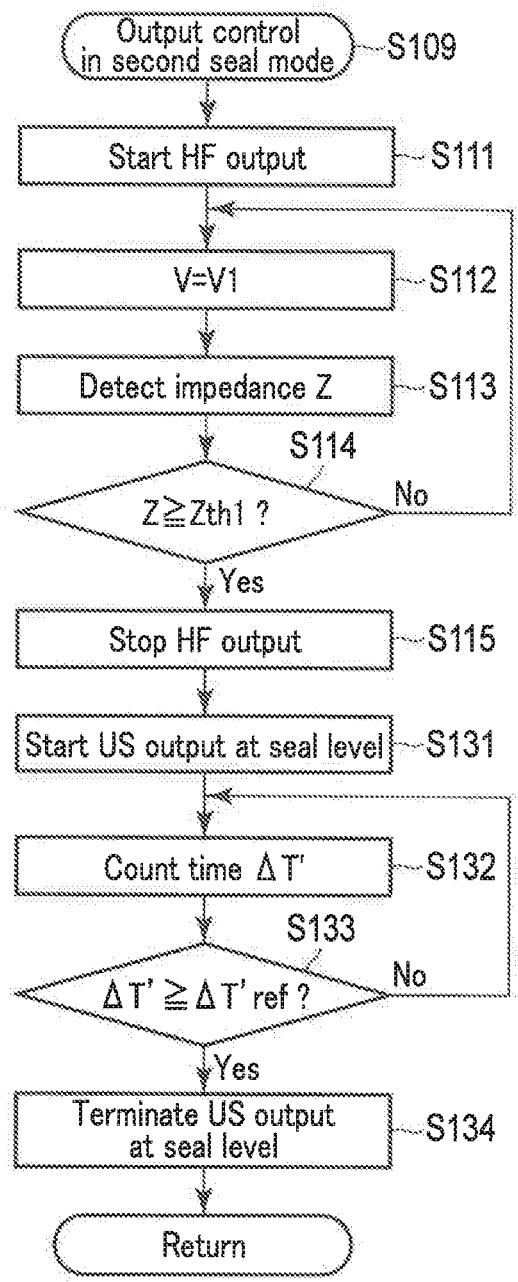
FIG. 11 is a flowchart illustrating a process in the second seal mode of the output control executed by the processor according to the third modification of the first embodiment.

In a third modification of the first embodiment, the processor 21 executes a process as illustrated in FIG. 11 in the second seal mode of the output control. In this modification, in the first seal mode of the output control, the processor 21 executes the same process as in the first embodiment (see FIG. 4). Furthermore, in the second seal mode of the output control, the processor 21 executes the processes of steps S111 through S115 in the same manner as in the first seal mode of the output control.

In the second seal mode, when the output of the electric energy from the energy output source 32 is stopped as a result of the process in step S115, the output controller 26 of the processor 21 starts the output of the electric energy from the energy output source 47 to the ultrasonic transducer 46 (step S131). Here, the energy output source 47 outputs the electric energy at a seal level having a low output level. That is, when the electric energy is output at the seal level, the output level is lower than the output of the electric energy at the above-described incision level. Thus, the electric energy supplied to the ultrasonic transducer 46 is lower, and the amplitude of the ultrasonic vibrations transferred to one of the grasping pieces 15 and 16 is smaller, in the output at the seal level than in the output at the incision level. Because the amount of frictional heat generated by the ultrasonic vibrations is small in the output at the seal level, the grasped blood vessel will not be incised by the frictional heat, but will only be sealed. In FIG. 11, the "HF output" denotes the high-frequency output of the electric energy from the energy output source 32 to the electrodes 27 and 28, and the "US output" denotes the ultrasonic output of the electric energy from the energy output source 47 to the ultrasonic transducer 46.

Here, a time (elapsed time) ΔT' is defined with reference to the time point of starting the output of the electric energy from the energy output source 47 at the seal level as a result of the process in step S131 (i.e., the time point of stopping the output from the energy output source 32 as a result of the process in step S115) being 0. When the output of the electric energy is started from the energy output source 47 at the seal level, the processor 21 starts counting the time ΔT' (step S132). The processor 21 determines whether the counted time ΔT' is greater than or equal to a reference time ΔT'ref (step S133). The reference time ΔT'ref may be set, for example, by the surgeon, or may be stored in the storage medium 22.

If the time ΔT' is shorter than the reference time ΔT'ref (No at step S133), the process returns to step S132, and the processes of step S132 and thereafter are successively executed. That is, the time ΔT' continues to be counted. If the time ΔT' is greater than or equal to the reference time ΔT'ref (Yes at step S133), the output controller 26 terminates the output of the electric energy from the energy output source 47 at the seal level (step S134). Here, the output of the electric energy from the energy output source 47 to the ultrasonic transducer 46 may be stopped. Alternatively, the output control may be automatically shifted to the incision mode so as to automatically change to a state in which the electric energy is output to the ultrasonic transducer 46 at the incision level (high output level). In one example, instead of the processes of step S132 and S133, the output controller 26 may stop the output of the electric energy at the seal level from the energy output source 47, in response to the release of the operation input of the operation button (energy operation input section) 18 (i.e. the operation input being turned off).

As described above, in the present modification, when the output controller 26 (processor 21) stops the output of the electric energy to the electrodes 27 and 28 in the second seal mode, the output controller 26 starts the output of the electric energy to the ultrasonic transducer 46. That is, the processor 21 controls the output of the electric energy from the energy output sources 32 and 47, based on the determination result of the tension, thereby switching the actuation state of the energy treatment instrument 2 between the first mode (first actuation mode) and the second mode (second actuation mode). In the present modification, the electric energy is output from the energy output source 47 only in the second seal mode. Thus, in the energy treatment instrument 2, the state of the treatment energy (high-frequency current and ultrasonic vibrations) applied from the energy application section (grasping pieces 15 and 16) to the grasped treatment target differs between the first mode and the second mode. Thus, in the second seal mode, even after the output of the electric energy to the electrodes 27 and 28 is stopped, the ultrasonic vibrations (frictional heat) seal the grasped blood vessel. That is, in the second seal mode, even in the state in which the impedance Z is increased, causing a resistance to the high-frequency current flow in the blood vessel, the blood vessel can still be sealed by the frictional heat generated by the ultrasonic vibrations. Thus, in comparison to the first seal mode, the performance of sealing the blood vessel by the treatment energy is enhanced in the second seal mode. Accordingly, when there is tension exerted onto the grasped blood vessel, the treatment is performed in the second seal mode, in which the performance of sealing the blood vessel using the treatment energy of the energy treatment instrument 2 of the treatment system 1 is higher than in the first seal mode. Thus, the blood vessel can be sealed to substantially the same degree as when there is no tension exerted onto the grasped blood vessel. By using the energy treatment instrument 2 of the treatment system 1, the performance of sealing the blood vessel as represented, for example, by the pressure resistance value of the sealed blood vessel (resistance of the blood flow to the sealed region), can be readily maintained even when there is tension exerted on the blood vessel.

In one modification, when the output of the electric energy from the energy output source 32 is stopped by the process in step S115 in the second seal mode, the output controller 26 of the processor 21 starts the output of the electric energy to the heater. At this time, the electric energy is output at the seal level having a lower output level than the above-described incision level. Thus, the electric energy supplied to the heater as the output at the seal level is smaller than the output at the incision level. With a small amount of heat generated by the heater as the output at the seal level, the grasped blood vessel is not incised by the heat of the heater, and therefore only sealing of the blood vessel is performed. In this modification, the blood vessel is sealed in the second seal mode by the heat of the heater in addition to the high-frequency current. That is, in the present modification, the state of the treatment energy (the high-frequency current and the heat of the heater) applied from the energy application section (grasping pieces 15 and 16) to the grasped treatment target differs between the first mode and the second mode in the energy treatment instrument 2. The performance of sealing the blood vessel by the treatment energy is therefore higher in the second seal mode than in the first seal mode. Thus, the same function and advantageous effects as in the third modification of the first embodiment can be obtained.

The output control of the electric energy, in which the performance of sealing the blood vessel by the treatment energy is increased when it is determined that there is tension exerted on the grasped blood vessel in comparison to when it is determined that there is no tension exerted on the blood vessel, may be adopted for an example in which a high-frequency current is not applied to the blood vessel, and only the treatment energy other than the high-frequency current (e.g., the ultrasonic vibration and the heat of the heater) is applied to the blood vessel. For instance, in one modification in which the electric energy is output to the ultrasonic transducer 46 at the seal level and the blood vessel is sealed by using only the ultrasonic vibrations, the processor 21 reduces the electric energy to be output from the energy output source 47 to the ultrasonic transducer 46, and increases the output time length of the electric energy to the ultrasonic transducer 46 in the second seal mode (the second mode of the energy treatment instrument 2), in comparison to the first seal mode (the first mode of the energy treatment instrument 2). In this manner, the time length of the ultrasonic vibrations being applied to the blood vessel is longer, and the performance of sealing the blood vessel by the ultrasonic vibrations is higher in the second seal mode (when it is determined that there is tension exerted on the blood vessel) than in the first seal mode (when it is determined that there is no tension exerted on the blood vessel). Furthermore, in one modification in which the electric energy is output to the heater at the seal level and the blood vessel is sealed by using only the heat of the heater, the processor 21 reduces the electric energy to be output from the energy output source to the heater, and increases the output time length of the electric energy to the heater in the second seal mode, in comparison with the first seal mode. As a result, the time length of the heat of the heater being applied to the blood vessel becomes longer, and the performance of sealing the blood vessel by the heat of the heater becomes higher in the second seal mode (when it is determined that there is tension exerted on the blood vessel) than in the first seal mode (when it is determined that there is no tension exerted on the blood vessel). With the energy treatment instrument 2 of the treatment system 1, the performance of sealing the blood vessel as represented, for example, by the pressure resistance value of the sealed blood vessel (resistance to the blood flow to the sealed region) can be easily maintained even when there is tension exerted on the grasped blood vessel.

In one modification, whether the processor 21 executes the output control in the first seal mode or in the second seal mode may be determined, for example, by the surgeon. In this modification, for example, two operation buttons, which serve as an energy operation input section, may be provided so that, when an operation is input from one of the operation buttons, the processor 21 (output controller 26) executes the output control of the electric energy in the first seal mode, and the energy treatment instrument 2 is actuated in the first mode (first actuation mode) for coagulating the treatment target. When an operation is input from the other operation button, the processor 21 executes the output control of the electric energy in the second seal mode, in which the performance of sealing the blood vessel by the treatment energy is higher than in the first seal mode. The energy treatment instrument 2 is thereby actuated in the second mode (second actuation mode) in which the treatment target is coagulated and the state of the treatment energy applied to the treatment target differs from the first mode. In the second mode, the performance of coagulating the treatment target by the treatment energy (the performance of sealing the blood vessel by the treatment energy) is higher than in the first mode. In this modification, a notification section (not shown) may be provided in the control device 3 configured to notify whether there is tension exerted on the grasped blood vessel (or whether the grasped blood vessel has been moved in a specific direction (e.g., toward the upper side) in the observation image). In one example, the notification section is an LED, and the LED is turned on when it is determined that there is tension exerted on the grasped blood vessel. In another example, the notification section may be a buzzer, a display screen, or the like.

In another modification, the display device 67 functions as a notification section, and at least one of an observation image and the optical flow of the grasped blood vessel is displayed on the display device 67. In this modification, the surgeon determines whether there is a tension exerted on the grasped blood vessel, based on the observation image and/or the optical flow displayed on the display device 67. Then, the surgeon determines which of the two operation buttons is to be operated to execute the operation input, and selects whether the processor 21 executes the output control in the first seal mode or in the second seal mode.

In a fourth modification of the first embodiment, in the seal treatment of the blood vessel, the processors 21 and 72 execute a process illustrated in FIG. 12. In the same manner as the above-described embodiment, the processors 21 and 72 execute the processes of steps S101 to S106 and S108 in the seal treatment of the blood vessel, in the present modification. If it is determined that there is no tension exerted on the grasped blood vessel (step S106), the processor 21 executes the output control of the electric energy in the seal mode (step S141). In the output control in the seal mode, the processor 21 executes, for example, the same process as the output control in the first seal mode of the first embodiment (see FIG. 4). The processor 21 executes the output control of the electric energy in the seal mode, and thereby the energy treatment instrument 2 is actuated in the first mode for coagulating the grasped treatment target (sealing the blood vessel). If it is determined that there is tension exerted on the grasped blood vessel (step S108), the processor 21 continues to stop the output of the electric energy, whether or not an operation is input from the operation button 18 (step S142). Here, the energy treatment instrument 2 is actuated in the second mode. That is, the output of the electric energy from the energy output sources 32 and 47 continues to be stopped. Thus, when it is determined that there is tension exerted on the grasped blood vessel (when it is determined that the blood vessel is moved in a specific direction in the observation image), no treatment energy such as high-frequency current is applied to the grasped blood vessel even if an operation is input from the operation button 18. In this modification, the processor 21 controls the output of the electric energy from the energy output source 32 based on the determination result of the tension, and thereby switches the actuation state of the energy treatment instrument 2 between the first mode (first actuation mode) and the second mode (second actuation mode). In this modification, the output of the electric energy from the energy output sources 32 and 47 is stopped in the second mode. Thus, the state of the treatment energy (high-frequency current, etc.) applied from the energy application section (grasping pieces 15 and 16) to the grasped treatment target in the energy treatment instrument 2 differs between the first mode and the second mode.

With the output control as described above in the present modification, no treatment energy is applied to the blood vessel when there is tension exerted on the grasped blood vessel. In other words, in the state in which the sealing performance may be affected, for example, in the state in which the blood vessel is being pulled to one side in a direction intersecting the extending direction of the blood vessel, no treatment energy is applied to the blood vessel. The treatment energy is applied to the blood vessel only in the state in which the sealing performance will be barely affected, for example when the blood vessel is not being pulled. Thus, the blood vessel is suitably sealed by using the treatment energy such as a high-frequency current, and a suitable treatment performance (sealing performance) is achieved.

In still another modification, the surgeon may decide whether or not to output the electric energy in the seal mode. In this modification, the above-described notification section is provided in, for example, the control device 3 or display device 67. When it is notified or determined that there is no tension exerted on the grasped blood vessel, the surgeon inputs an operation from the operation button 18 so that the processor 21 executes the output control in the seal mode. The electric energy is thereby output from the energy output sources 32 and 47, and the energy treatment instrument 2 is actuated in the first mode (first actuation mode). On the other hand, when it is notified or determined that there is tension exerted on the grasped blood vessel, the surgeon will not input an operation from the operation button 18. Thus, without any electric energy output from the energy output sources 32 and 47, the energy treatment instrument 2 is actuated in the second mode (second actuation mode) that is different from the first mode.

Second Embodiment

Next, a second embodiment of the present invention will be described with reference to FIGS. 13 to 15. In the second embodiment, the configuration of the first embodiment is modified as described below. The same parts as in the first embodiment are denoted by the same reference numerals, and the description of these parts is omitted.

Figure 13:
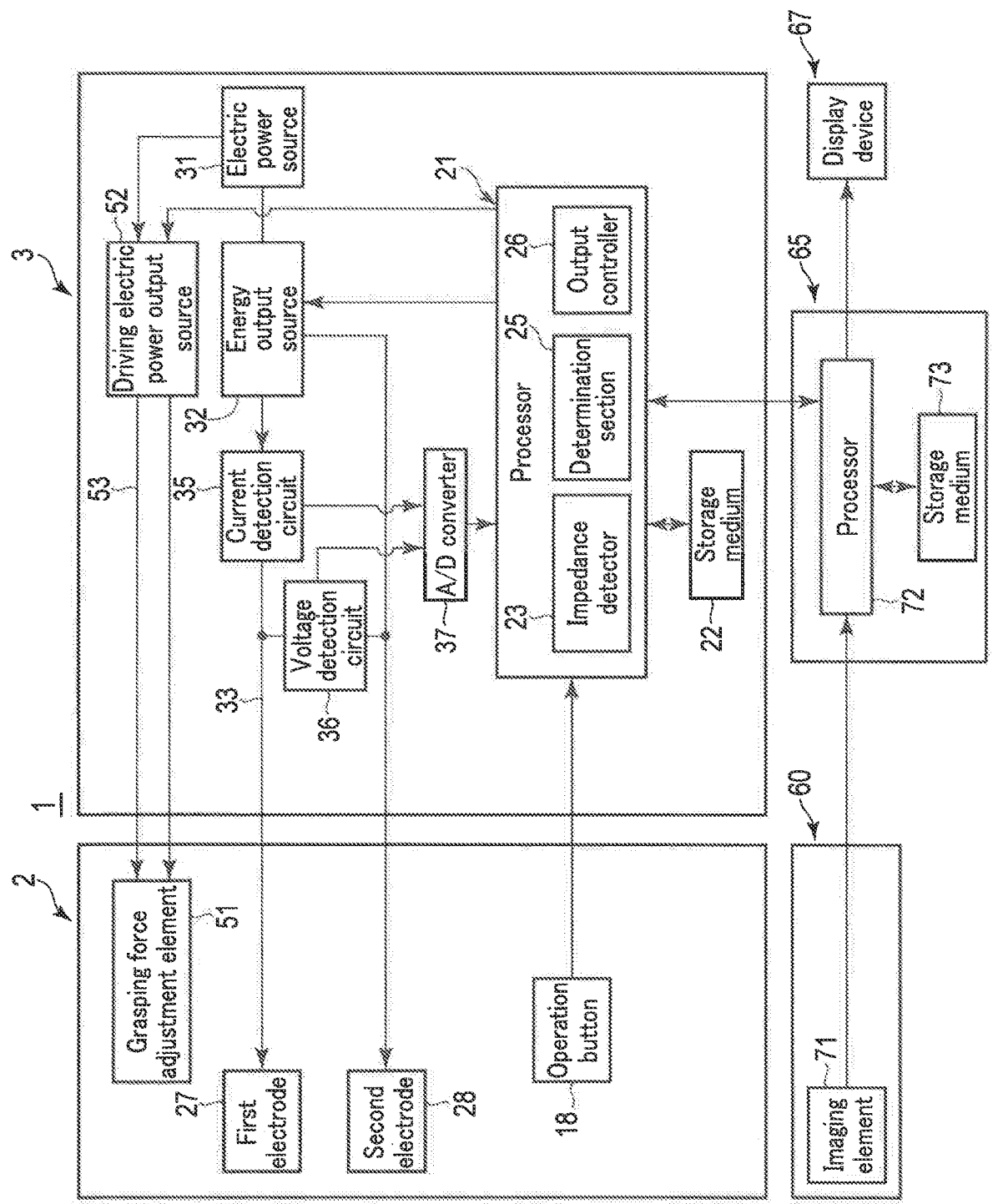
FIG. 13 is a block diagram illustrating a control configuration in a treatment system according to a second embodiment.

FIG. 13 is a diagram illustrating a control configuration in a treatment system 1 according to the present embodiment. In the present embodiment, a grasping force adjustment element 51 (grasping force adjuster) is provided in the energy treatment instrument 2, as illustrated in FIG. 13. A grasping force acting on the treatment target (blood vessel) between the grasping pieces 15 and 16 varies in accordance with a driving state of the grasping force adjustment element 51. That is, the grasping force acting on the treatment target between the grasping pieces 15 and 16 is adjusted by the grasping force adjustment element 51. In addition, in this embodiment, a driving electric power output source 52 is provided in the control device 3. The driving electric power output source 52 is electrically connected to the grasping force adjustment element 51 via an electricity supply path 53 extending inside the cable 10. Here, the driving electric power output source 52 may be formed integrally with the above-described energy output sources 32 and 47, or may be formed separately from the energy output sources 32 and 47.

The driving electric power output source 52 includes a converter circuit, an amplifier circuit, and the like, and converts the electric power from the electric power source 31 to the driving electric power for the grasping force adjustment element 51. The driving electric power output source 52 outputs the converted driving electric power, and the output driving electric power is supplied to the grasping force adjustment element 51 through the electricity supply path 53. The processor 21 controls the driving of the driving electric power output source 52, and controls the output of the driving electric power from the driving electric power output source 52. In this manner, the supply of the driving electric power to the grasping force adjustment element 51 is controlled, and the driving of the grasping force adjustment element 51 is controlled. According to the present embodiment, in accordance with the driving state of the grasping force adjustment element 51, the actuation state of the energy treatment instrument 2 is switched between the first mode (first actuation mode) and the second mode (second actuation mode). According to the present embodiment, the grasping force acting on the treatment target (blood vessel) between the grasping pieces 15 and 16 differs between the first mode and the second mode.

FIG. 14 is a diagram illustrating an example of the grasping force adjustment element 51. In the example illustrated in FIG. 14, a heater 55 and a volume change portion 56 are provided as the grasping force adjustment element 51 in the second grasping piece 16. The volume change portion 56 is formed of an electrically insulating material such as parylene, nylon, or ceramics. By closing the grasping pieces 15 and 16 relative to each other, the volume change portion 56 is brought into contact with the first grasping piece 15 (first electrode 27). In the state in which the volume change portion 56 is in contact with the first grasping piece 15, the electrodes 27 and 28 are spaced apart from each other, and are prevented from being in a contact with each other by the volume change portion 56. The volume change portion 56 is formed of a material having a high thermal expansion coefficient.

With the driving electric power output from the driving electric power output source 52 to the heater 55, the grasping force adjustment element 51 is driven, and heat is generated by the heater 55. With the heat generated by the heater 55, the temperature of the volume change portion 56 rises, as a result of which the volume change portion 56 expands (the volume of the volume change portion 56 increases). Because of the volume change portion 56 expanding in the state in which the blood vessel (treatment target) is grasped between the grasping pieces 15 and 16, the distance between the grasping pieces 15 and 16 decreases, and the grasping force acting on the treatment target between the grasping pieces 15 and 16 increases. In this example, the heat generated by the heater 55 is not used for coagulation or incision of the treatment target.

In another example, a Peltier element may be provided in place of the heater 55. With this arrangement, the driving electric power is output from the driving electric power output source 52 to the Peltier element, and the Peltier element thereby transfers the heat to the volume change portion 56 side. With the heat transferred by the Peltier element, the temperature of the volume change portion 56 rises, as a result of which the volume change portion 56 expands. Thus, as described above, in the state in which the blood vessel (treatment target) is grasped between the grasping pieces 15 and 16, the distance between the grasping pieces 15 and 16 decreases, and the grasping force of the treatment target between the grasping pieces 15 and 16 increases.

Next, the function and advantageous effects of the present embodiment will be described. FIG. 15 is a flowchart illustrating the process executed by the processors 21 and 72 in the seal treatment of the blood vessel using the treatment system 1 of the present embodiment. In the present embodiment, the processors 21 and 72 execute the processes of steps S101 to S106 and S108 in the seal treatment of the blood vessel in the same manner as the above-described embodiment and the like. Then, when it is determined that there is no tension exerted on the grasped blood vessel (step S106), the processor 21 continues to stop the output of the driving electric power from the driving electric power output source 52 to the grasping force adjustment element 51 (step S151). The grasping force adjustment element 51 is therefore not driven, and the volume change portion 56 does not expand. The grasping force of the treatment target between the grasping pieces 15 and 16 is thereby maintained. Furthermore, the processor 21 executes the output control of the electric energy from the energy output source 32 or the like in the seal mode (step S152). In the output control in the seal mode, the processor 21 executes, for example, the same process as the output control in the first seal mode of the first embodiment (see FIG. 4). In the state in which the output of the driving electric power from the driving electric power output source 52 to the grasping force adjustment element 51 is stopped by the processor 21 and the grasping force adjustment element 51 is not driven, the energy treatment instrument 2 is actuated in the first mode (first actuation mode) for coagulating the grasped treatment target (sealing the blood vessel).

On the other hand, if it is determined that there is tension exerted on the grasped blood vessel (step S108), the processor 21 starts to output the driving electric power from the driving electric power output source 52 to the grasping force adjustment element 51 (step S153). Thus, the grasping force adjustment element 51 is driven, and the volume change portion 56 expands. The grasping force acting on the treatment target between the grasping pieces 15 and 16 thereby increases. The processor 21 executes the output control of the electric energy from the energy output source 32 or the like in the seal mode (step S154). In the output control in the seal mode, the processor 21 executes, for example, the same process as the output control in the first seal mode of the first embodiment (see FIG. 4). When the output control in the seal mode ends, the processor 21 stops the output of the driving electric power from the driving electric power output source 52 to the grasping force adjustment element 51 (step S155). In the state in which the processor 21 causes the driving electric power output source 52 to output the driving electric power to the grasping force adjustment element 51 and thereby drives the grasping force adjustment element 51, the energy treatment instrument 2 is actuated in the second mode (second actuation mode) for coagulating the grasped treatment target (sealing the blood vessel), which is different from the first mode. As described above, in the present embodiment, the processor 21 controls the output of the driving electric power from the driving electric power output source 52 based on the determination result of the tension, thereby switching the actuation state of the energy treatment instrument 2 between the first mode (first actuation mode) and the second mode (second actuation mode). In the energy treatment instrument 2, the driving state of the grasping force adjustment element 51 differs between the first mode and the second mode. Thus, the grasping force of the treatment target (blood vessel) between the grasping pieces 15 and 16 differs between the first mode and the second mode.

In the present embodiment, under the control by the processor 21 as described above, the processor 21 increases the grasping force of the blood vessel (treatment target) between the grasping pieces 15 and 16 when it is determined that there is tension exerted on the grasped blood vessel, in comparison to when it is determined that there is no tension exerted on the blood vessel. That is, in the energy treatment instrument 2, the grasping force acting on the blood vessel (treatment target) between the grasping pieces 15 and 16 is larger in the second mode (second actuation mode) than in the first mode (first actuation mode). For this reason, even when there is tension exerted on the grasped blood vessel, the grasped blood vessel can be suitably sealed by increasing the grasping force acting on the blood vessel between the grasping pieces 15 and 16. That is, even when the blood vessel is grasped while being pulled to one side in the direction intersecting the extending direction of the blood vessel, the blood vessel can be suitably sealed using the treatment energy, and a suitable treatment performance (sealing performance) can be achieved.

Modifications of Second Embodiment

The grasping force adjustment element 51 is not limited to the above configuration. In one modification, for example, an electric motor and an abutment member are provided as the grasping force adjustment element 51. If this is the case, the handle 12 is brought into contact with the abutment member by closing the handle 12 relative to the grip 11, and the handle 12 is closed relative to the grip 11 to come up to a position at which the handle 12 abuts on the abutment member. In addition, the processor 21 (output controller 26) controls the output of the driving electric power from the driving electric power output source 52 to the electric motor, and thereby controls the driving of the electric motor. When the electric motor is driven, the abutment member is moved, and the position of the abutment member is changed. This changes the stroke of the handle at a time of closing the handle 12 relative to the grip 11. In this modification, the processor 21 adjusts the position of the abutment member, based on the determination result as to whether there is tension exerted on the grasped blood vessel so that the stroke of the handle 12 for closing is increased when it is determined that there is tension exerted on the grasped blood vessel (in the second mode of the energy treatment instrument 2), in comparison to when it is determined that there is no tension exerted on the grasped blood vessel (in the first mode of the energy treatment instrument 2). Thus, in this modification, the grasping force of the blood vessel (treatment target) between the grasping pieces 15 and 16 is increased when it is determined that there is tension exerted on the grasped blood vessel, in comparison to when it is determined that there is no tension exerted on the blood vessel.

If one of the grasping pieces 15 and 16 is formed by a rod member to be inserted through the sheath 6, a support member supporting the rod member on the most distal side within the sheath 6, and an electric motor or the like driven to move this support member, may be provided as the grasping force adjustment element 51. If this is the case, by driving the electric motor or the like in accordance with the determination result of tension being exerted or not exerted on the grasped blood vessel, the position where the rod member is supported by the support member can be changed. In this manner, with the treatment target (blood vessel) being grasped between the grasping pieces 15 and 16, the amount of deflecting of the distal portion (one of the grasping pieces 15 and 16) of the rod member varies, and the grasping force between the grasping pieces 15 and 16 varies. In addition, the control for adjusting the grasping force as in the second embodiment may be suitably used, as long as the grasping force adjustment element 51 is provided for varying the grasping force acting on the treatment target (blood vessel) between the grasping pieces 15 and 16.

In another modification, an operation button or the like may be provided as a driving operation input section to output the driving electric power from the driving electric power output source 52. In this modification, the surgeon may decide as to whether or not the driving electric power should be output. In this modification, the above-described notification section is provided in the control device 3 or display device 67, for example. When it is notified or determined that there is no tension exerted on the grasped blood vessel, the surgeon will not input an operation from the operation button (driving operation input section). The driving electric power is therefore not output from the driving electric power output source 52 to the grasping force adjustment element 51 (heater 55), and the volume change portion 56 does not expand. Thus, the energy treatment instrument 2 is actuated in the first mode (first actuation mode). On the other hand, when it is notified or determined that there is tension exerted on the grasped blood vessel, the surgeon inputs an operation from the operation button 18. In response, the driving electric power is output from the driving electric power output source 52 to the grasping force adjustment element 51 (heater 55), and the volume change portion 56 expands by the heat generated by the heater 55. Thus, the energy treatment instrument 2 is actuated in the second mode (second actuation mode), and the grasping force acting on the treatment target between the grasping pieces 15 and 16 increases.

Other Modifications

In one modification, any one of the first embodiment and its modifications and any one of the second embodiment and its modifications may be combined. If this is the case, when it is determined that there is no tension exerted on the grasped blood vessel, the processor 21 executes the output control of the electric energy from the energy output sources 32 and 47 in the first seal mode, and applies the treatment energy to the blood vessel. When it is determined that there is tension exerted on the grasped blood vessel, the processor 21 executes the output control of the electric energy from the energy output sources 32 and 47 in the second seal mode, in which the performance of sealing the blood vessel by the treatment energy is higher than in the first seal mode, and the processor 21 applies the treatment energy to the blood vessel. That is, in this modification, the performance of sealing the blood vessel by the treatment energy is higher in the second mode of the energy treatment instrument 2 than in the first mode, in a manner similar to the first embodiment. Furthermore, in this modification, the processor 21 increases the grasping force acting on the treatment target between the grasping pieces 15 and 16 when it is determined that there is tension exerted to the grasped blood vessel (the second mode of the energy treatment instrument 2), in comparison to when it is determined that there is no tension applied to the grasped blood vessel (the first mode of the energy treatment instrument 2).

Figure 15:
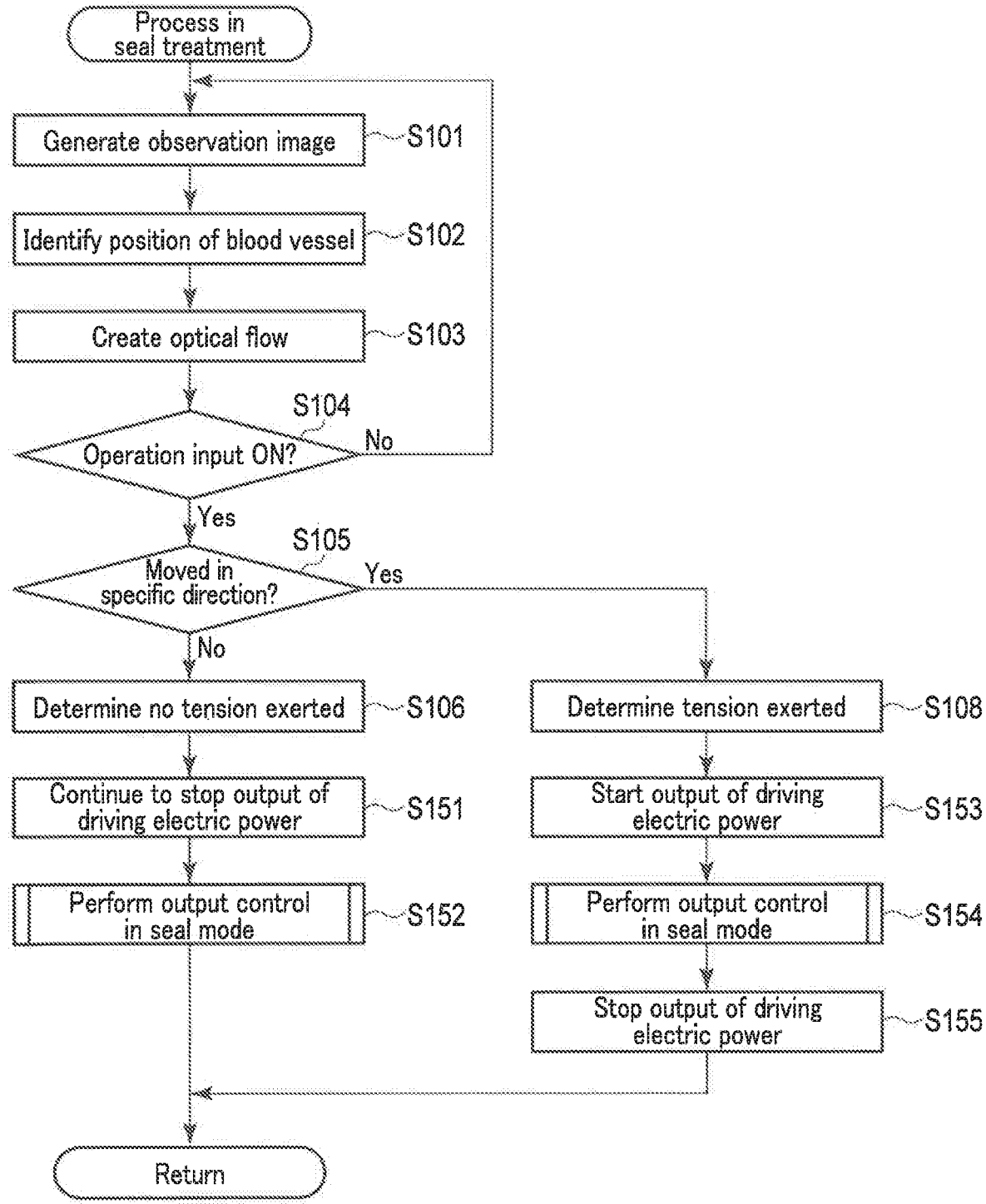
FIG. 15 is a flowchart illustrating a process executed by the processor in the seal treatment of the blood vessel using the treatment system according to the second embodiment.

The processes illustrated in FIGS. 3, 12, and 15 may be executed by either the processor 21 of the control device (energy control device) 3 or the processor 72 of the image processing device 65. In one modification, the processor 21 of the control device 3 may create an optical flow of the grasped blood vessel (step S103), and in another modification, the processor 72 of the image processing device 65 may determine as to whether the grasped blood vessel has been moved to a specific direction (e.g. toward the upper side) in the observation image (step S105). In still another modification, an integral device having the functions of both the control device 3 and the image processing device 65 may be provided in the treatment system 1. In this modification, the processes illustrated in FIGS. 3, 12, and 15 are executed by a processor provided in this integral device.

In the above-described embodiments, an energy treatment instrument (2) of a treatment system (1) includes a first grasping piece (15), and a second grasping piece (16) configured to open and close relative to the first grasping piece (15) and configured to grasp a treatment target between the first grasping piece (15) and the second grasping piece (16). The actuation state of the energy treatment instrument (2) is switched between a first mode for coagulating a treatment target when there is tension exerted on a grasped treatment target and a second mode for coagulating a treatment target when there is no tension exerted. In the treatment system (1), an energy output source (32 or 47, or both 32 and 47) is configured to output the electric energy that is to be supplied to the energy treatment instrument (2), and is configured to apply the treatment energy to the treatment target grasped between the first grasping piece (15) and the second grasping piece (16) when the electric energy is supplied to the energy treatment instrument (2). An observation element (60) is configured to observe a grasped treatment target. A processor (21, 72) is configured to determine whether there is tension exerted on the grasped treatment target, based on an observation image obtained by the observation element (60). The processor (21, 72) is configured to execute at least one of controlling an output of the electric energy from the energy output source (32 or 47, or both 32 and 47), based on a determination result of the tension; and increasing a grasping force acting on the treatment target between the first grasping piece (15) and the second grasping piece (16) when it is determined that there is tension exerted, in comparison to when it is determined that there is no tension exerted.

A characteristic feature is added below.
(Addendum 1)
A treatment method, comprising:
closing a first grasping piece and a second grasping piece with respect to each other, thereby grasping a treatment target between the first grasping piece and the second grasping piece;
observing the grasped treatment target;
supplying electric energy from an energy output source to an energy treatment instrument, and applying treatment energy to the grasped treatment target between the first grasping piece and the second grasping piece;
determining whether there is tension exerted on the grasped treatment target based on an observation image of the treatment target; and
controlling output of the electric energy from the energy output source based on a determination result of the tension, and/or increasing a grasping force on the treatment target between the first grasping piece and the second grasping piece when it is determined that there is tension exerted, in comparison with when it is determined that there is no tension exerted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment system comprising:
an energy treatment instrument, the energy treatment instrument including a first grasping piece, and a second grasping piece configured to close with respect to the first grasping piece and grasp a treatment target together with the first grasping piece;
an energy output source configured to output electric energy that is to be supplied to the energy treatment instrument, and configured to supply the electric energy to the energy treatment instrument, thereby applying treatment energy to the treatment target grasped between the first grasping piece and the second grasping piece;
an observation element configured to observe the grasped treatment target; and
a processor configured to create an optical flow of the treatment target observed by the observation element, and configured to switch an actuation state of the energy treatment instrument between a first mode for treating the treatment target and a second mode for treating the treatment target that is different from the first mode, based on the optical flow.

2. The treatment system according to claim 1, wherein the processor is configured to determine whether there is tension exerted on the treatment target, based on the optical flow, and configured to switch the actuation state of the energy treatment instrument based on a determination result, between the first mode, which is adopted when there is no tension exerted on the treatment target, and the second mode, which is adopted when there is tension exerted.

3. The treatment system according to claim 2, wherein at least one of the first grasping piece and the second grasping piece includes an energy application section configured to apply the treatment energy to the grasped treatment target.

4. The treatment system according to claim 3, wherein a state of applying the treatment energy from the energy application section to the grasped treatment target differs between the first mode and the second mode.

5. The treatment system according to claim 2, wherein a grasping force acting on the treatment target between the first grasping piece and the second grasping piece differs between the first mode and the second mode.

6. The treatment system according to claim 2, wherein the processor is configured to reduce the electric energy to be output and configured to increase an output duration of the electric energy when determining that there is tension exerted.

7. The treatment system according to claim 2, wherein after the output of the electric energy is started, the processor is configured to suspend the output of the electric energy and configured to resume the output of the electric energy after the output of the electric energy is suspended, when determining that there is tension exerted, thereby intermittently outputting the electric energy for a plurality of times.

8. The treatment system according to claim 2, wherein the processor is configured to detect an impedance between the first grasping piece and the second grasping piece, and when determining that there is no tension exerted, the processor is configured to stop the output of the electric energy in response to the impedance having reached or exceeded a first impedance threshold, and when determining that there is tension exerted, the processor stops the output of the electric energy in response to the impedance having reached or exceeded a second impedance threshold that is greater than the first impedance threshold.

9. The treatment system according to claim 2, wherein when determining that there is tension exerted, the processor is configured to stop the output of the electric energy.

10. The treatment system according to claim 2, wherein the processor is configured to determine that there is tension exerted on the treatment target, when determining that the grasped treatment target is moved in a specific direction based on the optical flow.

11. The treatment system according to claim 2, wherein the first grasping piece includes a first electrode, the second grasping piece includes a second electrode, and the energy output source is configured to supply the output electric energy to the first electrode and the second electrode, thereby allowing a high-frequency current to flow as the treatment energy through the treatment target between the first grasping piece and the second grasping piece.

12. The treatment system according to claim 2, wherein the processor is configured to increase a grasping force acting on the treatment target between the first grasping piece and the second grasping piece when determining that there is tension exerted in comparison to when determining there is no tension exerted, and thereby switches the actuation state of the energy treatment instrument between the first mode and the second mode.

13. A control device for controlling a medical instrument, the medical instrument including a pair of grasping pieces configured to open and close with respect to each other, the control device comprising a processor configured to: determine whether there is tension exerted on a treatment target grasped by the pair of grasping pieces based on an optical flow of a treatment target observed by an observation element; select, based on a determination result, a control mode from a first mode, which is adopted when there is no tension exerted on the treatment target, and a second mode, which is adopted when there is tension; and control the medical instrument based on the selected control mode.

14. A treatment method, comprising: by use of an energy treatment instrument, which includes a first grasping piece, and a second grasping piece configured to open and close with respect to the first grasping piece, grasping a treatment target between the first grasping piece and the second grasping piece; outputting electric energy that is to be supplied to the energy treatment instrument, and applying treatment energy to the treatment target grasped between the first grasping piece and the second grasping piece; and creating an optical flow of the treatment target by use of an observation element, and switching an actuation state of the energy treatment instrument between a first mode for treating the treatment target and a second mode for treating the treatment target that is different from the first mode, based on the optical flow.

15. The treatment method according to claim 14, further comprising: determining, based on the optical flow, whether there is tension exerted on the treatment target, and switching the actuation state of the energy treatment instrument between the first mode, which is adopted when there is no tension exerted on the treatment target, and the second mode, which is adopted when there is tension exerted, based on a determination result.

* * * * *